United States Patent
Akao

(10) Patent No.: US 10,869,974 B2
(45) Date of Patent: Dec. 22, 2020

(54) INHALATION COMPONENT GENERATING DEVICE, CONTROL CIRCUIT, AND CONTROL METHOD AND CONTROL PROGRAM OF INHALATION COMPONENT GENERATING DEVICE

(71) Applicant: JAPAN TOBACCO INC., Tokyo (JP)

(72) Inventor: Takeshi Akao, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/592,439

(22) Filed: Oct. 3, 2019

(65) Prior Publication Data

US 2020/0108213 A1    Apr. 9, 2020

(30) Foreign Application Priority Data

Oct. 4, 2018   (JP) .................. 2018-189511

(51) Int. Cl.
*H05B 1/02*       (2006.01)
*A61M 15/06*   (2006.01)
(Continued)

(52) U.S. Cl.
CPC ........... *A61M 15/06* (2013.01); *A24F 47/008* (2013.01); *A24B 15/167* (2016.11);
(Continued)

(58) Field of Classification Search
CPC ............ A61M 5/06; A61M 2205/3334; A61M 2205/3368; A61M 2205/3653;
(Continued)

(56) References Cited

U.S. PATENT DOCUMENTS 9,423,152 B2 *   8/2016   Ampolini ............... A24F 47/008
9,498,000 B2 *  11/2016   Kuczaj .................. H05B 3/0014
(Continued)

FOREIGN PATENT DOCUMENTS

CA        3054492 A1    9/2018
CN       10539802 A     2/2016
(Continued)

OTHER PUBLICATIONS

Japanese Office Action issued in Japanese Patent Application No. 2018-192625 dated Jan. 15, 2019.
(Continued)

*Primary Examiner* — Mark H Paschall
(74) *Attorney, Agent, or Firm* — Birch, Stewart, Kolasch & Birch, LLP

(57) ABSTRACT

An inhalation component generating device includes: a power supply; a load that evaporates or atomizes an inhalation component source by power from the power supply; and a control circuit that performs control based on an output of a temperature sensor. The control circuit performs: a process (a) of calculating power supply temperature on the basis of the output of the temperature sensor; and a process (b1) of determining whether the power supply temperature is in a first temperature range, and performing deterioration diagnosis on the power supply only in a case where the power supply temperature is in the range.

11 Claims, 11 Drawing Sheets

(51) Int. Cl.
  *A24F 47/00* (2020.01)
  *A24B 15/167* (2020.01)
(52) U.S. Cl.
  CPC .............. *A61M 2205/3334* (2013.01); *A61M 2205/3368* (2013.01); *A61M 2205/3653* (2013.01); *A61M 2205/50* (2013.01); *A61M 2205/8206* (2013.01)
(58) Field of Classification Search
  CPC ....... A61M 2205/50; A61M 2205/8206; A24F 47/008; H05B 1/02; H05B 1/0288
  USPC ........ 219/494, 492, 497, 486, 505; 131/328, 131/329, 271–273, 194; 392/395, 492
  See application file for complete search history.

(56) References Cited

U.S. PATENT DOCUMENTS

| | | | |
|---|---|---|---|
| 10,031,183 B2 * | 7/2018 | Novak, III | A24F 47/008 |
| 2013/0340775 A1 * | 12/2013 | Juster | A24F 47/008 |
| | | | 131/273 |
| 2015/0053217 A1 * | 2/2015 | Steingraber | A24F 47/008 |
| | | | 131/329 |
| 2015/0346285 A1 | 12/2015 | Igarashi et al. | |
| 2016/0366939 A1 | 12/2016 | Alarcon et al. | |
| 2017/0027234 A1 | 2/2017 | Farine et al. | |
| 2017/0033568 A1 | 2/2017 | Holzherr | |
| 2017/0238606 A1 | 8/2017 | Matsumoto et al. | |
| 2017/0250552 A1 * | 8/2017 | Liu | H02J 7/007 |
| 2017/0251728 A1 * | 9/2017 | Peleg | G05D 23/24 |
| 2017/0280779 A1 * | 10/2017 | Qiu | G05D 23/24 |
| 2019/0252888 A1 | 8/2019 | Holzherr | |

FOREIGN PATENT DOCUMENTS

| | | |
|---|---|---|
| EP | 3207811 A1 | 8/2017 |
| JP | 6-242192 A | 9/1994 |
| JP | 2003-100356 A | 4/2003 |
| JP | 2009-183105 A | 8/2009 |
| JP | 2010-282878 A | 12/2010 |
| JP | 2016-525345 A | 8/2016 |
| JP | 2017-514463 A | 6/2017 |
| JP | 2017-518733 A | 7/2017 |
| WO | WO 2016/076178 A1 | 5/2016 |
| WO | WO 2018/163262 A1 | 9/2018 |

OTHER PUBLICATIONS

Eurasian Search Report, dated Mar. 5, 2020, for Eurasian Application No. 201992068/26: along with an English translation.

European Search Report, dated Mar. 6, 2020, for European Application No. 19201431.4.

Chinese Office Action and Search Report for Chinese Application No. 201910951181.9, dated Aug. 28, 2020, with English translation.

* cited by examiner

INHALATION COMPONENT GENERATING DEVICE, CONTROL CIRCUIT, AND CONTROL METHOD AND CONTROL PROGRAM OF INHALATION COMPONENT GENERATING DEVICE

CROSS-REFERENCE TO RELATED APPLICATIONS

This application is based upon and claims the benefit of priority from prior Japanese patent application No. 2018-189511, filed on Oct. 4, 2018, the entire contents of which are incorporated herein by reference.

TECHNICAL FIELD

The present invention relates to an inhalation component generating device, a control circuit, and a control method and a control program of the inhalation component generating device, and particularly, to an inhalation component generating device, a control circuit, and a control method and a control program of the inhalation component generating device capable of performing deterioration diagnosis on a power supply at an appropriate timing, thereby improving the accuracy of deterioration diagnosis.

BACKGROUND ART

Recently, instead of traditional cigarettes, inhalation component generating devices for generating an inhalation component by evaporating or atomizing a flavor source such as tobacco or an aerosol source have been proposed. Such an inhalation component generating devices has a load for evaporating or atomizing a flavor source and/or an aerosol source, a power supply for supplying power to the load, a control circuit for performing operation control on the device, and so on.

With respect to determination on the degree of battery consumption of such a device, for example, in Patent Literature 1, a technology for determining whether battery exchange is necessary, and the like on the basis of the amount of change in voltage during discharge is disclosed. Also, in Patent Literature 2, a method of appropriately determining whether to perform charging of the battery of an aerosol generating device, and what charging rate charging will be performed at, and so on, on the basis of the ambient temperature of a charging device is disclosed.

[Patent Literature 1] JP-A-2017-514463
[Patent Literature 2] JP-A-2017-518733

Patent Literature 1 discloses the technology for determining whether battery exchange is necessary by measuring battery voltage as described above, which is a technology related to deterioration estimation on a battery, however in Patent Literature 1, the relation between performance of deterioration estimation and the range of temperature is not disclosed at all.

Also, in Patent Literature 2, a technology for setting some temperature ranges in advance, and determining to or not to perform charging and performing change of the charging rate on the basis of the relation with those temperature ranges is disclosed; however, this technology is not focused on the relation between performance of deterioration estimation and the range of temperature, either.

Meanwhile, the inventors of this application found that it is difficult to discriminate between a decrease in the output of a power supply attributable to deterioration of the power supply and a decrease in the output of the power supply in the case where the temperature of the power supply is not appropriate, on the basis of earnest examination. On the basis of this knowledge, the inventors of this application further found that if deterioration diagnosis is performed only in the case where the temperature of the power supply is within a certain range, the accuracy of deterioration diagnosis drastically improves. Therefore, an object of the present invention is to provide an inhalation component generating device, a control circuit, and a control method and a control program of the inhalation component generating device capable of performing deterioration diagnosis on a power supply at an appropriate timing, thereby improving the accuracy of deterioration diagnosis.

SUMMARY OF INVENTION

According to an aspect of the invention, there is provided an inhalation component generating device comprising: a power supply; a load that evaporates or atomizes an inhalation component source by power from the power supply; and a control circuit that performs control based on an output of a temperature sensor, wherein the control circuit performs: a process (a) of calculating power supply temperature based on the output of the temperature sensor; and a process (b) of determining whether the power supply temperature is in a first temperature range, and performing deterioration diagnosis on the power supply only in a case where the power supply temperature is in the range.

Description of Terms

The term "inhalation component generating device" may mean a device for generating an inhalation component by evaporating or atomizing a flavor source such as tobacco or an aerosol source, or may be a single-housing product, or may be a device consisting of a plurality of components (units) which can be connected to be used as one product.

The term "power supply" means a unit for serving as the source of electric energy, and includes a battery, a capacitor, and so on. As the battery, for example, a secondary battery such as a lithium-ion secondary battery can be used. The secondary battery may be a battery including a positive electrode, a negative electrode, a separator separating the positive electrode and the negative electrode from each other, and an electrolytic solution or an ionic liquid. The electrolyte or the ionic liquid may be, for example, a solution containing an electrolyte. In the lithium-ion secondary battery, the positive electrode is made of a positive electrode material such as lithium oxide, and the negative electrode is made of a negative electrode material such as graphite. The electrolytic solution may be, for example, an organic solvent containing a lithium salt. Examples of the capacitor include an electric double-layer capacitor and so on. However, the power supply is not limited to them, and any other secondary battery such as a nickel-hydride secondary battery, a primary battery, or the like may be used.

The term "load" means a component which consumes energy in an electric circuit, and is especially used in this application to indicate a component for mainly generating an inhalation component. In the load, a heating means such as a heat generator is included, and for example, an electric resistance heat generator, an induction heating (IH) means, and so on can be included. Also, a means for generating an inhalation component by an ultrasonic wave, a means for generating an inhalation component by a piezoelectric element, an atomizer, and so on can be included. In the case where the load is referred to as being a "load group", besides a load for generating an inhalation component, other components such as an element for producing light, sound, vibration, or the like can be included in the load group. In the case where a communication module and so on are provided, they can be included in the load group. Meanwhile, a microcomputer and so on in an electric circuit are strictly elements which obtain energy by applying a very small current; however, in this application, it is assumed that they are not included in the load group.

The term "aerosol" means a dispersion of fine liquid or solid particles in the air.

With respect to a "deterioration diagnosis function", in general, examples of battery deterioration include a decrease in capacity and an increase in resistance. The deterioration diagnosis function may be, for example, a function of acquiring the voltage value of the power supply for diagnosis of a decrease in capacity, and determining whether the acquired value is equal to or larger than the lower limit value of a predetermined reference range.

DESCRIPTION OF EMBODIMENTS

An embodiment of the present invention will be described below with reference to the drawings. However, specific structures and electric circuits to be described below are merely examples of the present invention, and the present invention is not necessarily limited to them. Also, hereinafter, structural parts basically having the same function will be described with the same reference symbol or reference symbols corresponding to each other; however, for ease of explanation, sometimes the reference symbols will be omitted. Although the configurations of some parts of a device are different between a certain drawing and other drawings, it should be noted that they are not essential differences in the present invention and every configuration can be used.

1. Configuration of Device

Figure 1:
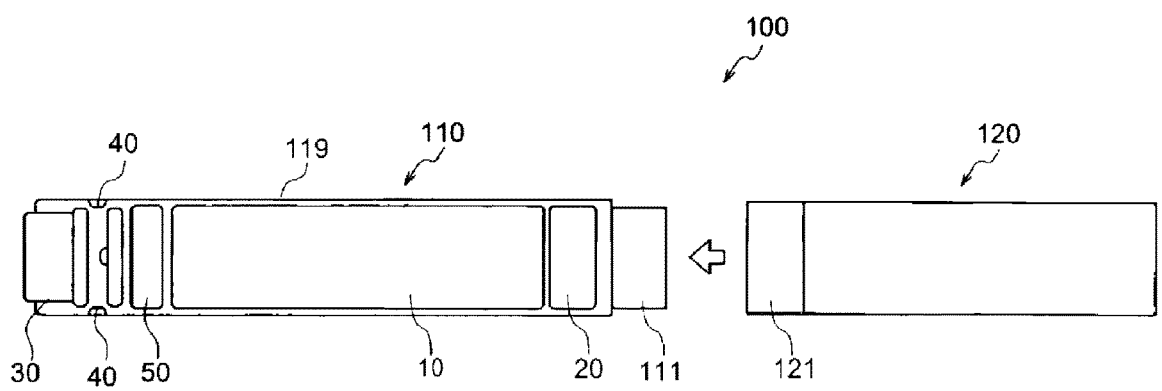
FIG. 1 is a cross-sectional view schematically illustrating the configuration of an inhalation component generating device according to an embodiment of the present invention.
Figure 2:
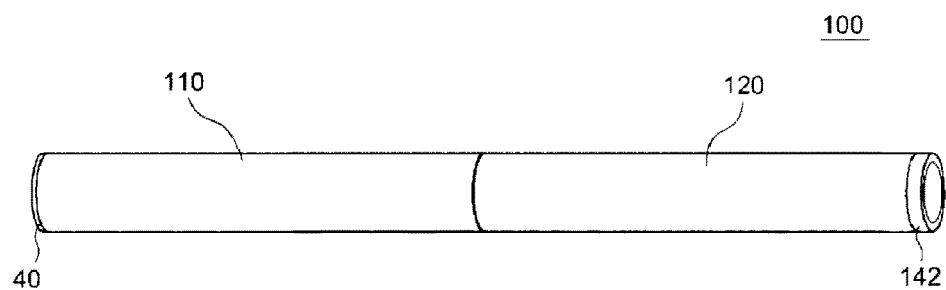
FIG. 2 is a perspective view illustrating an example of the external appearance of the inhalation component generating device.

An inhalation component generating device 100 of the present embodiment includes a power supply unit 110, and a cartridge unit 120 configured to be attachable to and detachable from the power supply unit, as shown in FIG. 1 and FIG. 2. In the present embodiment, an example in which the power supply unit 110 and the cartridge unit 120 are separately configured is shown; however, as the inhalation component generating device of the present invention, they may be integrally configured.

The overall shape of the inhalation component generating device 100 is not particularly limited, and may have various shapes. For example, as shown in FIG. 2, the inhalation component generating device may be made such that the overall shape becomes a rod shape. Specifically, the inhalation component generating device 100 becomes a single rod shape when the power supply unit 110 and the cartridge unit 120 are connected in the axial direction. If the overall shape of the device is made a single rod shape as described above, a user can perform inhalation like the user smokes a traditional cigarette. In the example of FIG. 2, an end part shown on the right side is an inhalation port part 142, and at the opposite end part, a light emitting unit 40 for emitting light according to the operation state of the device and so on is provided. The inhalation component generating device may be configured such that the user attaches a mouthpiece (not shown in the drawings) to the inhalation port part 142 for use and perform inhalation. The specific dimensions of the device are not particularly limited, and as an example, the diameter may be about 15 mm to 25 mm, and the total length may be about 50 mm to 150 mm, such that the user can use the device with a hand.

(Power Supply Unit)

The power supply unit 110 includes a case member 119, a power supply 10 installed in the case member, an inhalation sensor 20, a control circuit 50, and so on, as shown in FIG. 1. The power supply unit 110 further include a push button 30 and the light emitting unit 40. However, not all of these individual elements are necessarily essential components of the inhalation component generating device 100, and one or more elements may be omitted. Also, one or more elements may be provided in the cartridge unit 120, not in the power supply unit 110.

The case member 119 may be a cylindrical member, and although its material is not particularly limited, the case member may be made of a metal or a resin.

The power supply 10 may be a rechargeable secondary battery such as a lithium-ion secondary battery or a nickel hydride battery (Ni-MH). The power supply 10 may be a primary battery or a capacitor instead of a secondary battery. The power supply 10 may be a power supply provided in the power supply unit 110 so as to be exchangeable, or may be a power supply built in the power supply unit by assembling. The number of power supplies 10 may be one or more.

The inhalation sensor 20 may be a sensor for outputting a predetermined output value (for example, a voltage value or a current value), for example, according to the flow and/or flow rate of gas which passes there. This inhalation sensor 20 is used to detect a user's puffing action (inhaling action). As the inhalation sensor 20, various sensors can be used, and for example, a capacitor microphone sensor, a flow sensor, or the like can be used.

The push button 30 is a button which can be operated by the user. Although the button is referred to as the push button, the button is not limited to a component having a button part which moves when it is pushed, and may be an input device such as a touch button. The arrangement position of the push button 30 also is not particularly limited, and the push button may be provided at an arbitrary position on the housing of the inhalation component generating device 100. As an example, the push button 30 may be provided on the side surface of the case member 119 of the power supply unit 110 such that the user can easily operate it. A plurality of push buttons 30 (input devices for receiving inputs from the user) may be provided.

The light emitting unit 40 includes one or more light sources (for example, LEDs), and is configured to emit light in a predetermined pattern at a predetermined timing. For example, in an embodiment, it is preferable that the light emitting unit be configured to emit light in a plurality of colors. Examples of the functions of the light emitting unit 40 include a function of notifying the user of the operation status of the device, a function of notifying the user of occurrence of an abnormality if the abnormality occurs, and so on. Also, in consideration of those functions, as a notifying device which is provided in the inhalation component generating device 100, besides the light emitting unit, for example, one of a vibration device for producing vibration, an audio device for producing sound, a display device for displaying predetermined information, and so on, or a combination of them may be used. As an example, the light emitting unit 40 may be provided at an end part of the power supply unit 110. In the inhalation component generating device 100, if the light emitting unit 40 provided at the opposite end part to the end part where the inhalation port part 142 is provided emits light according to a user's puffing action, the user can easily inhale an inhalation component like the user smokes a traditional cigarette.

Figure 3:
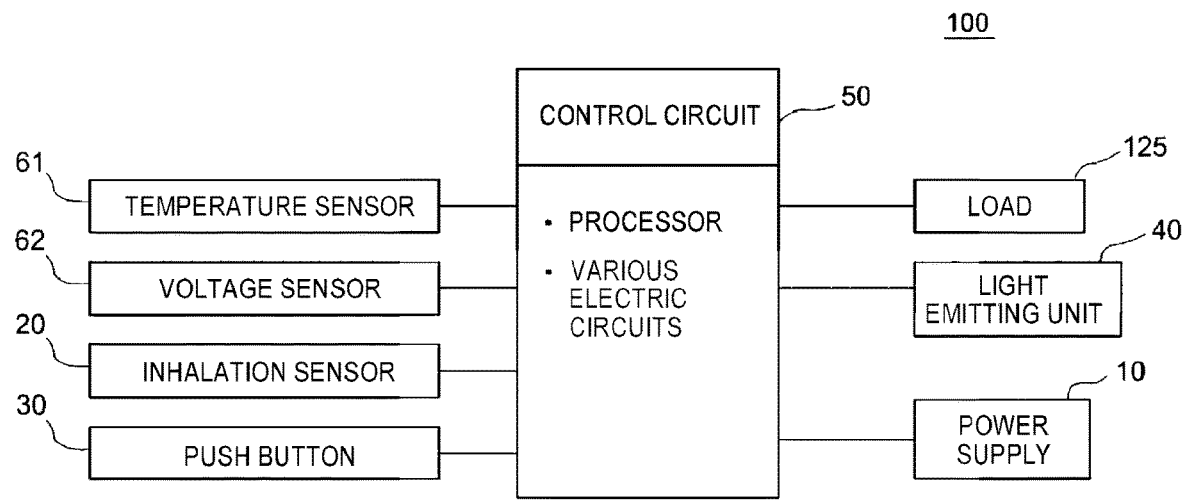
FIG. 3 is a block diagram illustrating an example of the configuration of the inhalation component generating device.

FIG. 3 is a block diagram illustrating an example of the configuration of the inhalation component generating device. As shown in FIG. 3, the inhalation component generating device 100 includes a temperature sensor 61, a voltage sensor 62, and so on, besides the above-mentioned components.

The temperature sensor 61 is a sensor for acquiring or estimating the temperature of a predetermined object provided in the inhalation component generating device 100. The temperature sensor 61 may be a sensor for measuring the temperature of the power supply 10, or may be a sensor for measuring the temperature of an object different from the power supply 10. Also, instead of preparing a dedicated temperature sensor, for example, a temperature detector assembled in a predetermined component of the electric circuit may be used. A specific process based on the output of the temperature sensor 61 will be described below. As the temperature sensor 61, for example, a thermistor, a thermocouple, a resistance thermometer, an IC temperature sensor, or the like can be used; however, the temperature sensor is not limited thereto. The number of temperature sensors 61 is not limited to one, and may be two or more.

The voltage sensor 62 is a sensor for measuring power supply voltage as an example. A sensor for measuring predetermined voltage other than the voltage of the power supply may be provided. A specific process based on the output of the voltage sensor 62 will be described below. The number of voltage sensors 62 also is not limited to one, and may be two or more.

The inhalation component generating device 100 may further include a radio communication device (not shown in the drawings) and/or a communication port (not shown in the drawings) for making a connection with an external device possible, and so on according to the needs. For example, the inhalation component generating device may be configured such that information on the status of the power supply, information on inhalation, and so on can be transmitted to an external device via them.

(Cartridge Unit)

Figure 4:
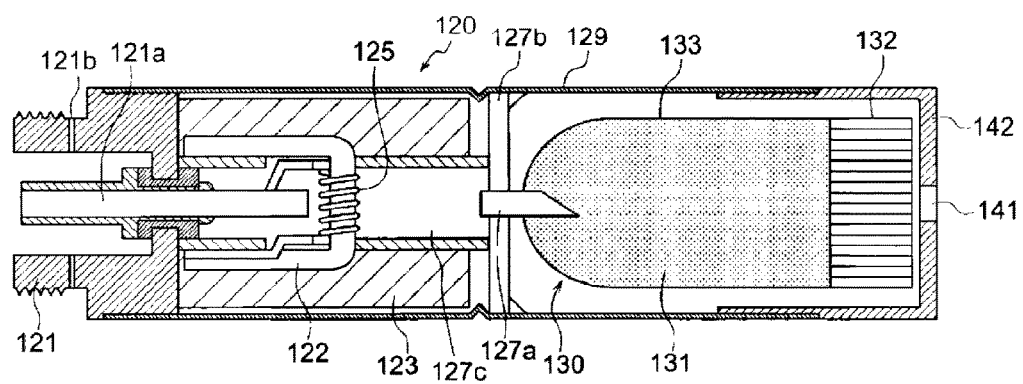
FIG. 4 is a cross-sectional view illustrating an example of the internal configuration of a cartridge unit.

The cartridge unit 120 is a unit having an inhalation component source therein, and includes a case member 129, a reservoir 123, a flavor unit 130, a load 125 for evaporating or atomizing the inhalation component source, and so on, as shown in FIG. 1 and FIG. 4. However, not all of the above-mentioned elements are necessarily essential components of the inhalation component generating device 100. Particularly, in the present embodiment, an example in which both of the reservoir 123 for generating an aerosol and the flavor unit 130 for generating a flavor component (to be described below in detail) are provided will be described; however, only one of them may be provided.

According to the general function of the cartridge unit 120, as an example, first, as a first stage, an aerosol source contained in the reservoir 123 is evaporated or atomized by the operation of the load 125. Subsequently, as a second stage, the generated aerosol flows in the flavor unit 130, such that a smoking flavor component is added, and is finally inhaled by the mouth of the user.

The case member 129 (see FIG. 4) may be a cylindrical member, and although its material is not particularly limited, the case member may be made of a metal or a resin. The cross section shape of the case member 129 may be the same as that of the case member 119 of the power supply unit 110. It has been described that the cartridge unit 120 can be connected to the power supply unit 110. Specifically, as an example, a connection part 121 provided at one end of the cartridge unit 120 may be physical connected to a connection part 111 provided at one end of the power supply unit 110. In FIG. 4, the connection part 121 is shown as a screw part; however, the present invention is not necessarily limited thereto. Instead of a connection using the screw parts, the connection part 111 and the connection part 121 may be magnetically joined. When the connection parts 111 and 121 are connected, the electric circuit in the power supply unit 110 and the electric circuit in the cartridge unit 120 may be electrically connected (which will be described in detail).

Inside the connection part 121, as shown in FIG. 4, a cylindrical member to form an inflow hole for introducing air into the unit is provided so as to extend in the axial direction of the case member 129. Also, at the connection part 121, one or more holes 121*b* are formed so as to extend in the radial direction, such that the outside air can be introduced through the hole 121*b*. The inflow hole may be formed in the connection part 111 of the power supply unit 110, not in the connection part 121 of the cartridge unit 120. Alternatively, inflow holes may be provided in both of the connection part 111 of the power supply unit 110 and the connection part 121 of the cartridge unit 120.

The reservoir 123 is a storage member for storing the aerosol source which is liquid at room temperature. The reservoir 123 may be a porous member which is made of a material such as a resin web. As the aerosol source, a source which is solid at room temperature also can be used. Herein, the form in which the aerosol source is stored in the reservoir 123 will be mainly described; however, in the reservoir 123, a flavor source may be stored.

As the aerosol source, for example, a polyhydric alcohol called glycerin or propylene glycol, water, and so on can be used. The aerosol source may not contain any flavor component. Alternatively, the aerosol source may contain a tobacco raw material or an extract separated from a tobacco raw material, which emits a smoking flavor component when it is heated.

As an example, the load 125 may be a heating element such as a heater, an ultrasonic element for generating, for example, fine droplets by an ultrasonic wave, or the like. Examples of the heating element include a heating resistor (for example, a heating wire), a ceramic heater, an induction heating type heater, and so on. However, the load 125 may be a load for generating the flavor component from the flavor source.

The structure around the reservoir 123 will be described in more detail. In the example of FIG. 4, a wick 122 is provided so as to be in contact with the reservoir 123, and the load 125 is provided so as to surround a part of the wick 122. The wick 122 is a member for sucking the aerosol source from the reservoir 123 using capillarity. The wick 122 may be, for example, glass fiber, a porous ceramic, or the like. When the part of the wick 122 is heated, the aerosol source stored therein is evaporated or atomized. Also, in an embodiment in which a flavor source is stored in the reservoir 123, the flavor source is evaporated or atomized.

In the example of FIG. 4, as the load 125, a heating wire formed in a spiral shape is provided. However, the load 125 is not necessarily limited to a specific shape as long as it can generate the inhalation component, and can be formed in an arbitrary shape.

The flavor unit 130 is a unit having the flavor source stored therein. As a specific configuration, various configurations can be used, and the flavor unit is not particularly limited. For example, as the flavor unit 130, an exchangeable cartridge may be provided. In the example of FIG. 4, the flavor unit 130 has a cylindrical member 131 in which the flavor source is filled. More specifically, this cylindrical member 131 includes a film member 133 and a filter 132.

The flavor source is configured with a raw material piece which is a plant material and adds a smoking flavor component to the aerosol. As the raw material piece which constitutes the flavor source, a compact made by forming the tobacco material such as shredded tobacco or a tobacco raw material into a grain shape can be used. Alternatively, as the flavor source, a compact made by forming the tobacco raw material into a sheet shape may be used. Also, the raw material piece to constitute the flavor source may be configured with a plant (such as mint or a herb) other than tobacco. To the flavor source, a flavoring agent may be added.

In the present embodiment, inside the cartridge unit 120, a breaking unit 127a is provided, as shown in FIG. 4, such that the film member 133 of the flavor unit 130 can be broken by the breaking unit 127a. Specifically, the breaking unit 127a is a cylindrical hollow noodle, and is configured so as to be able to stick its leading end side into the film member 133. The breaking unit 127a may be held by a partition member 127b for separating the cartridge unit 120 and the flavor unit 130. The partition member 127b is, for example, a polyacetal resin. When the breaking unit 127a and the flavor unit 130 are connected, one flow path is formed inside the cartridge unit 120, and the aerosol, air, and so on flows in the flow path.

Specifically, as shown in FIG. 4, the flow path is composed of an inflow hole 121a formed in the reservoir 123, an inner passage 127c connected thereto, a passage in the breaking unit 127a, a passage in the flavor unit 130, and an inhalation hole 141 (to be described below in detail). Also, in an embodiment, it is preferable that a mesh having such a density that the flavor source can not pass through it be provided inside the breaking unit 127a which is a hollow noodle. The inhalation component generating device 100 may include the inhalation port part 142 having the inhalation hole 141 formed for the user to inhale the inhalation component. The inhalation port part 142 may be configured to be attachable to and detachable from the inhalation component generating device 100, or may be configured integrally with the inhalation component generating device 100 so as not to be separable.

Figure 5:
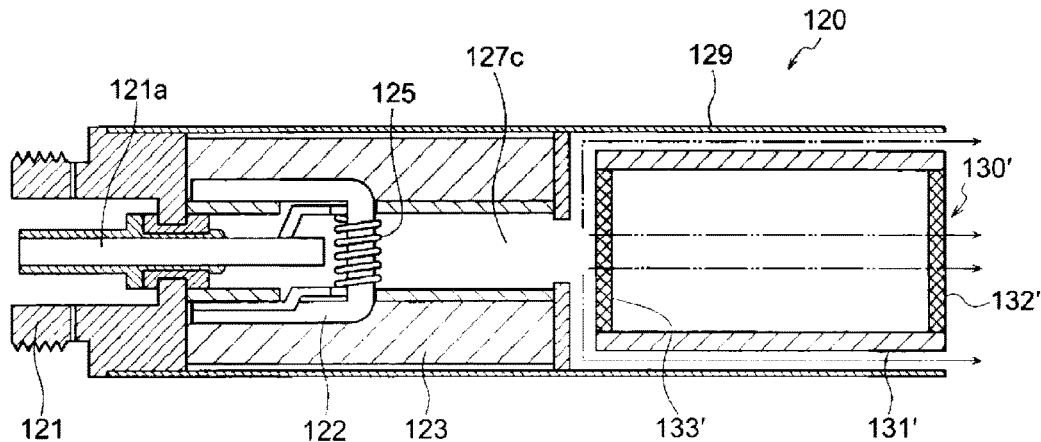
FIG. 5 is a cross-sectional view illustrating another example of the internal configuration of the cartridge unit.

Also, the flavor unit may be, for example, a unit having a structure as shown in FIG. 5. A flavor unit 130' has a flavor source contained in a cylindrical member 131', and a film member 133' provided at one open end of the cylindrical member 131', and a filter 132' provided at the other open end. The cylindrical member 131' may be provided in the cartridge unit 120 so as to be exchangeable. The other structural parts of FIG. 5 are the same as those of FIG. 4, so a repetitive description thereof will not be made. Also, in the example of FIG. 5, between the outer periphery of the cylindrical member 131' of the flavor unit 130' and the inner periphery of the case member 129, there is a gap; however, such a gap may not be formed. In this case, the air which is sucked passes through the cylindrical member 131'. As the flavor unit 130', various types of units containing different kinds of flavor sources may be commercially supplied such that it is possible to set one in the inhalation component generating device 100 according to the user's preference and perform inhalation. Also, the flavor unit 130' may be configured such that when the flavor unit 130' is connected to the cartridge unit 120, an end part of the flavor unit 130' is exposed from the case member 129. According to this configuration, since the exchangeable flavor unit 130' serves as the inhalation port part 142, the user can use the inhalation component generating device 100 in a sanitary way.

(Control Circuit)

Referring to FIG. 3 again, the control circuit 50 of the inhalation component generating device 100 may be a circuit including a processor having a memory and a CPU (both of which are not shown in the drawings), various electric circuits, and so on. The processor needs only to be a component for performing various processes regardless of its name, and may be a component referred to, for example, as an MCU (Micro Controller Unit), a microcomputer, a control IC, a control unit, or the like. As the control circuit 50, a single control circuit may be configured to perform control on the functions of the inhalation component generating device 100, or a plurality of control circuits may be configured to share in performing various functions.

Hereinafter, a configuration in which a charger 200 is provided separately from the inhalation component generating device 100 will be described as an example. In this case, in the device, a first control circuit may be provided, and in the charger, a second control circuit may be provided, such that predetermined functions can be performed by the individual control circuits. Meanwhile, as another configuration example of the inhalation component generating device 100, it also is possible to incorporate a charger function in the main body of the device, and in this case, a single control circuit may be configured. Like this, in the present embodiment, according to the physical configuration of the device and so on, a plurality of control circuits may be configured, and how to divide up a variety of control among the control circuits can be appropriately changed.

(Electric Circuit Configuration)

Figure 6:
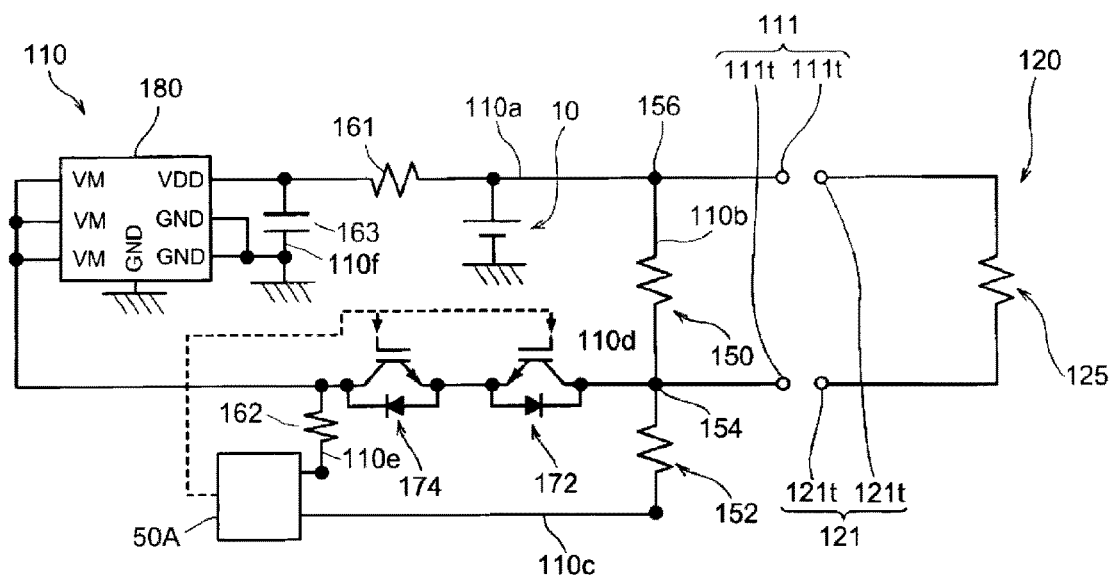
FIG. 6 is a view illustrating the electric circuit of the inhalation component generating device (in the state where a power supply unit and the cartridge unit are connected).

An example of the specific circuit configuration of the inhalation component generating device 100 of the present embodiment will be described below with reference to the drawings. As shown in FIG. 6, as the entire electric circuit of the inhalation component generating device 100, the circuit in the power supply unit 110 and the circuit in the cartridge unit 120 are provided such that they can be connected.

In the circuit of the cartridge unit 120, the load 125 is provided, and both ends of the load 125 are connected to a pair of electric terminals 121t. In the present embodiment, the pair of electric terminals 121t constitute the connection part 121 in terms of electric connection.

Figure 7:
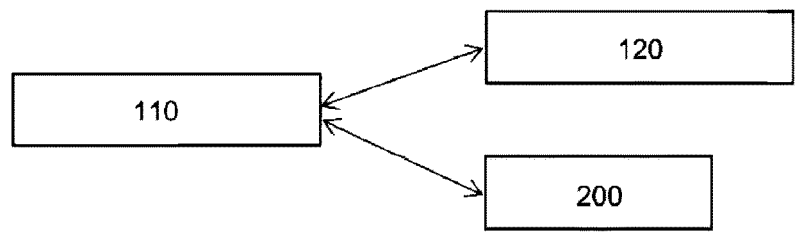
FIG. 7 is a schematic diagram illustrating the cartridge unit and a charger configured to be attachable to and detachable from the power supply unit.

As the circuit of the power supply unit 110, a control unit (a control IC) 50A, the power supply 10, a protection circuit 180, a first switch 172, a second switch 174, and so on are provided. As schematically shown in FIG. 7, the circuit of the power supply unit is configured such that to the circuit of the power supply unit 110, the circuit of the cartridge unit 120 described above is connected, and the circuit of the charger 200 (to be described below in detail) also can be connected.

Referring to FIG. 6 again, in the circuit of the power supply unit 110, the high potential side of the power supply 10 and the control unit 50A are connected via a path 110a, a path 110b, and a path 110c. The path 110a connects the high potential side of the power supply 10 and a node 156, and the path 110b connects the node 156 and a node 154, and the path 110c connects the node 154 and the control unit 50A. From the node 154, a path 110d is drawn, and by the path 110d, the node 154 and the protection circuit 180 are connected. On the path 110d, the two switches 172 and 174 are provided.

Between the part of the path 110a connected to the high potential side of the power supply 10 and the protection circuit 180, a resistor 161 is provided. On the path 110b, a first resistor 150 is provided, and on the path 110c, a second resistor 152 is provided. In this example, moreover, one of a pair of electric terminals 111t is connected to the node 156, and the other is connected to the node 154. Also, the control unit 50A and a part of the path 110d between the second switch 174 and the protection circuit 180 are connected by a path 110e, and on this path 110e, a resistor 162 is provided. The protection circuit 180 and the path 110a also are connected by a path 110f, and on this path 110f, a capacitor 163 is provided. In an embodiment, it is preferable that the resistance values of the first resistor 150 and the second resistor 152 be known, although the present invention is not limited thereto. The first resistor 150 may be a resistor known to the control unit 50A and an external unit. Similarly, the second resistor 152 may be a resistor known to the control unit 50A and the external unit. Also, the electric resistance value of the first resistor 150 and the electric resistance value of the second resistor 152 may be the same.

The first switch 172 electrically connects and disconnects the power supply 10 and the load 125. The first switch 172 may be configured with, for example, a MOSFET. The first switch 172 may be a switch serving as a so-called discharging FET. The switching of the first switch 172 is controlled by the control unit 50A. Specifically, if the first switch 172 is closed (i.e. it is turned on), power is supplied from the power supply 10 to the load 125; whereas if the switch 172 is opened (i.e. it is turned off), power is not supplied.

Switching of the first switch 172 may be controlled such that PWM (Pulse Width Modulation) on the load 125 is performed. However, instead of PWM control, PFM (Pulse Frequency Modulation) control may be performed. The duty ratio for PWM control and the switching frequency for PFM control may be adjusted according to various parameters such as the voltage value of the power supply 10. The specific circuit configuration related to the first switch 172 is not necessarily limited to a configuration to be described below, and may include a parasitic diode. This parasitic diode may be configured such that when any external unit such as the charger is not connected, the direction in which the current from the power supply 10 flows into the parasitic diode via the node 154 becomes the reverse direction.

The second switch 174 is electrically connected to the node 154 via the first switch 172. The second switch 174 also may be configured with, for example, a MOSFET, and be controlled by the control unit 50A. Specifically, the second switch 174 may be able to transition between an open state for shutting off the current from the low potential side of the power supply 10 to the high potential side and a closed state for flowing the current from the low potential side of the power supply 10 to the high potential side. Also, the second switch 174 may include a parasitic diode in which the direction in which the current for charging the power supply 10 flows becomes the reverse direction.

In the above-described circuit configuration, the current from the power supply 10 mainly passes through the node 156, the load 125, the node 154, and the switch 172 in the order, and flows back to the power supply 10, whereby the load 125 is heated. Also, a part of the current from the power supply 10 passes through the resistor 150. Therefore, if the resistance value of the resistor 150 is set to be significantly larger than the resistance value of the load 125, it is possible to suppress the loss from being caused by the current flowing in the resistor 150.

(Circuit Configuration of Charger)

Now, an example of the specific circuit configuration of the charger 200 side will be described below with reference to FIG. 8. Also, in FIG. 8, the circuit configuration of the power supply unit 110 side is the same as that of FIG. 6.

The outer shape of the charger 200 is not limited, and can be set to an arbitrary shape. As an example, the charger 200 may have a shape similar to a USB (Universal Serial Bus) memory having a USB terminal which can be connected to a USB port. As another example, the charger 200 may have a cradle shape for holding the power supply unit, or a case shape for storing the power supply unit. In the case of configuring the charger 200 in the cradle shape or the case shape, it is preferable that an external power supply 210 be installed inside the charger 200 and the charger have such size and weight that the user can carry the charger.

Figure 8:
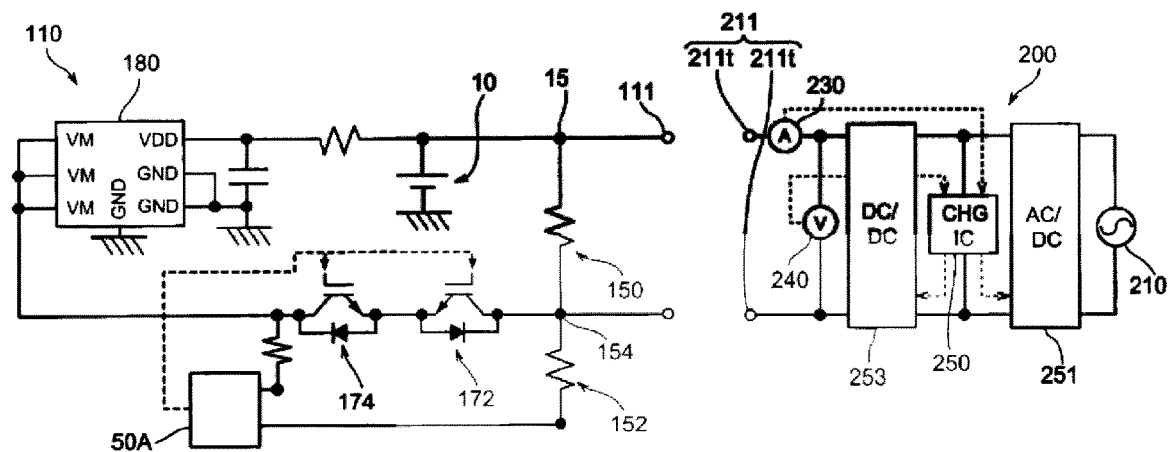
FIG. 8 is a view illustrating the electric circuit of the inhalation component generating device (in the state where the power supply unit and the charger are connected).

As shown in FIG. 8, as the circuit of the charger 200, a charging control unit (a charging control IC) 250, an inverter 251 for converting AC to DC, a converter 253 for stepping up or down the output voltage of the inverter 251, and so on are provided. The charger 200 may a charger including a charging power supply 210 provided therein for supplying charging power, or may use another device or a commercial power supply as an external power supply. Also, in the case where the charging power supply 210 is provided inside the charger 200 and outputs direct current, the inverter 251 may be omitted. Moreover, in the charger 200, a current sensor 230 for reading the value of charging current which is supplied to the power supply 10, and a voltage sensor 240 for acquiring the voltage difference between a pair of electric terminals 211t (connection parts 211) are provided. The voltage sensor 240 may be configured to be able to acquire the voltage value which is applied to the first resistor 150, in cooperation with the control circuit 50 and the switches 172 and 174.

The charging control unit 250 may be a unit having one or more functions including, for example, detection of a connection of the power supply unit 110, determination on the type of a connection object, and charging control based on the output value of the current sensor and/or the output value of the voltage sensor. However, instead of the charger 200, the control unit 50A of the inhalation component generating device 100 may be configured to perform one or more of those functions. The details of the above-mentioned functions will be described below.

2. Operation Control

Examples of the functions of the inhalation component generating device 100 include the followings.

(a1) Power Supply Control
(a2) Light Emission Control
(a3) Operation Control based on Temperature of Power Supply
(a4) Deterioration Diagnosis Function
(b1) Detection of Connection of Charger
(b2) Charging control Hereinafter, these functions will be described in the order.

(a1) Power Supply Control

The control circuit 50 has a function of performing an operation of supplying power to the load 125 on the basis of a request signal from a request sensor. The request sensor means a sensor capable of outputting, for example, a signal for requesting the operation of the load 125, namely, the sensor which outputs a generation request of an inhalation component. Specifically, the request sensor may be, for example, the push button 30 which can be pushed by the user, or the inhalation sensor 20 for detecting an inhaling action of the user. In other words, the control circuit 50 may be configured to perform a predetermined operation in response to pushing of the push button 30 and/or in response to the detection result of the inhalation sensor 20. The value related to the amount of operation of the load 2 may be measured by a predetermined counter.

With respect to end of power supply, the following control may be performed. In other words, the control circuit 50 determines whether the end timing of power supply to the load 125 has been detected, and ends the power supply in the case where the end timing has been detected. The control circuit 50 may measure the value related to the amount of operation of the load 125 (such as at least one of the amount of power supplied to the load, the operation time of the load, the consumption of the inhalation component source, and so on). More specifically, the end timing of power supply may be a timing when the inhalation sensor 20 has detected the end of an operation for using the load. For example, the end timing may be a timing when the end of an inhaling action of the user has been detected. Also, if release of the push button 30 from pushing is detected, power supply may be ended.

Also, end of power supply based on a cutoff time may be performed. In other words, at a timing when a predetermined cutoff time has passed in the course of power supply, power supply may be ended. In order to realize control based on a cutoff time, a cutoff time (in a range between 1.0 sec and 5.0 sec, preferably between 1.5 sec and 3.0 sec, and more preferably between 1.5 sec and 2.5 sec) determined on the basis of the time required for a general user to perform one inhaling action may be set.

Figure 9:
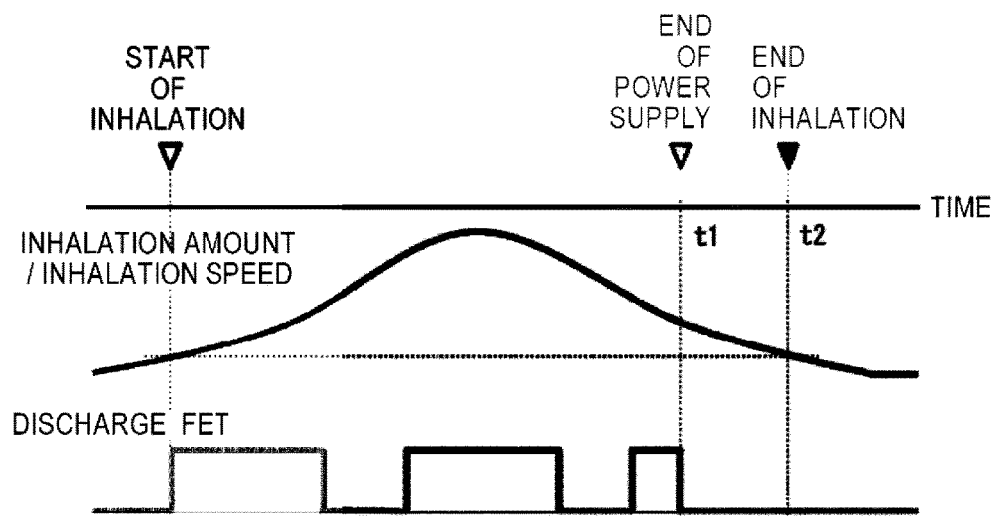
FIG. 9 is a view illustrating the relation between voltage which is applied to a load and an inhaling action.

An example of the cutoff time will be described in brief with reference to FIG. 9. The horizontal axis represents time, and the upper part shows change in the inhalation amount, and the lower part shows a discharge FET signal (corresponding to the waveform of the voltage which is applied to the load). In this example, first, when it is determined on the basis of the output of the inhalation sensor 20 (the inhalation amount or the inhalation speed) that inhalation has been started, power supply to the load is started. In FIG. 9, a time t2 is a timing when inhalation ends. In the case of using the cutoff time, although completion of inhalation is actually determined at the time t2, after the predetermined cutoff time (here, a time t1) passes, power supply is forcibly ended. If the cutoff time is set as described above, it is possible to reduce variation in the amount of aerosol generation whenever power is supplied. Therefore, it is possible to improve user's aerosol inhalation experience. Also, since continuous power supply to the load 125 for a long time is suppressed, it is possible to extend the life of the load 125.

Also, the control circuit 50 may be configured to be able to acquire values related to the amount of operation of the load during one puffing action and derive the cumulative value of the acquired values. In other words, the control circuit measures the amount of power supply to the load, the operation time of the load, and so on during one puffing action. As the operation time may be the sum of times when a power pulse is applied. Also, the control circuit may be configured to be able to measure the amount of inhalation component source consumed by one puffing action. The consumption of inhalation component source can be estimated, for example, from the amount of power supplied to the load. In the case where the inhalation component source is liquid, the consumption of inhalation component source may be derived on the basis of at least the weight of the inhalation component source remaining in the reservoir, or may be derived on the basis of at least the output of a sensor which measures the height of the liquid level of the inhalation component source. The amount of operation of the load during one puffing action may be derived on the basis of at least the temperature of the load (for example, at least one of the highest temperature of the load, the amount of heat generated by the load, and so on in the period of the puffing action).

Figure 10:
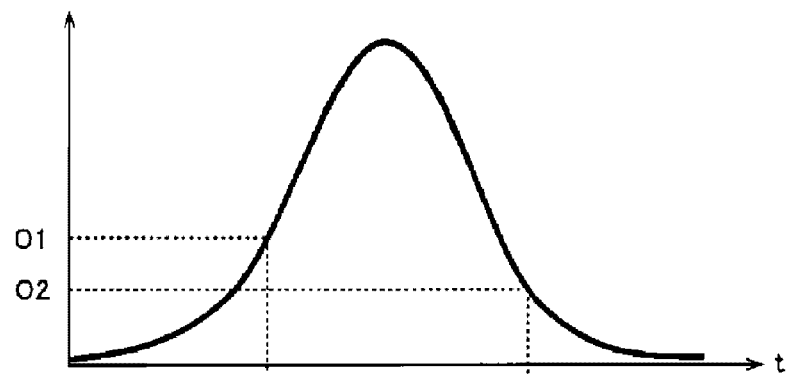
FIG. 10 is a view schematically illustrating the relation between the output value of an inhalation sensor and voltage which is applied to the load.
Figure 10:
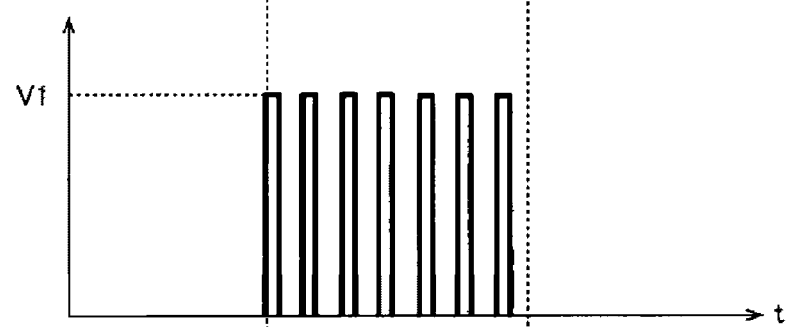
Figure 10:
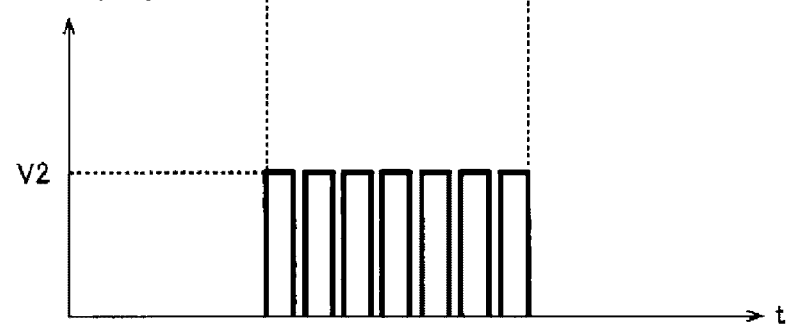

An additional description of the specific operation example based on the output of the inhalation sensor will be made with reference to FIG. 10. FIG. 10 is a view schematically illustrating the relation between the output value of the inhalation sensor and the voltage which is applied to the load. In this example, the control circuit 50 detects whether the output value of the inhalation sensor is equal to or larger than a first reference value O1, or not, and in the case where the output value is equal to or larger than the reference value, the control circuit determines that an inhaling action is being performed. This timing triggers a power supply request. The control circuit detects whether the output value of the inhalation sensor is equal to or smaller than a second reference value O2, or not, and in the case where the output value is equal to or smaller than the reference value, the control circuit determines that it's the end timing of power supply.

As an example, the control circuit 50 may be configured to detect inhalation only in the case where the absolute value of the output value of the inhalation sensor is equal to or larger than the first reference value O1. Since the detection using the second reference value O2 is detection for performing a transition from the state in which the load is already operating to the state in which the load is not operating, the second reference value O2 may be smaller than the first reference value O1.

With respect to the operation of the load, for example, in the case where the power-supply voltage value is relatively high, the pulse width during PWM control may be set to be narrower (see the middle part of the graph of FIG. 10), and in the case where the power-supply voltage value is relatively low, the pulse width may be set to be wider (the lower part of FIG. 10). Basically, the power-supply voltage value decreases as the charge amount of the power supply decreases. Therefore, in an embodiment, it is preferable to adjust the amount of power according to the power-supply voltage value on all such occasions. According to this control method, for example, it is possible to make the effective value of voltage (power) to be applied to the load in the case where the power-supply voltage value is relatively high same or substantially same as that in the case where the power-supply voltage value is relatively low. Also, it is preferable to perform PWM control using a higher duty ratio in the case where the power-supply voltage value is lower. According to this control method, regardless of the residual amount of the power supply, it becomes possible to appropriately adjust the amount of aerosol to be generated during a puffing action. If the amount of aerosol which is generated during a puffing action is almost uniformized, it is possible to improve user's aerosol inhalation experience.

(a2) Light Emission Control on LED and Others

Figure 11:
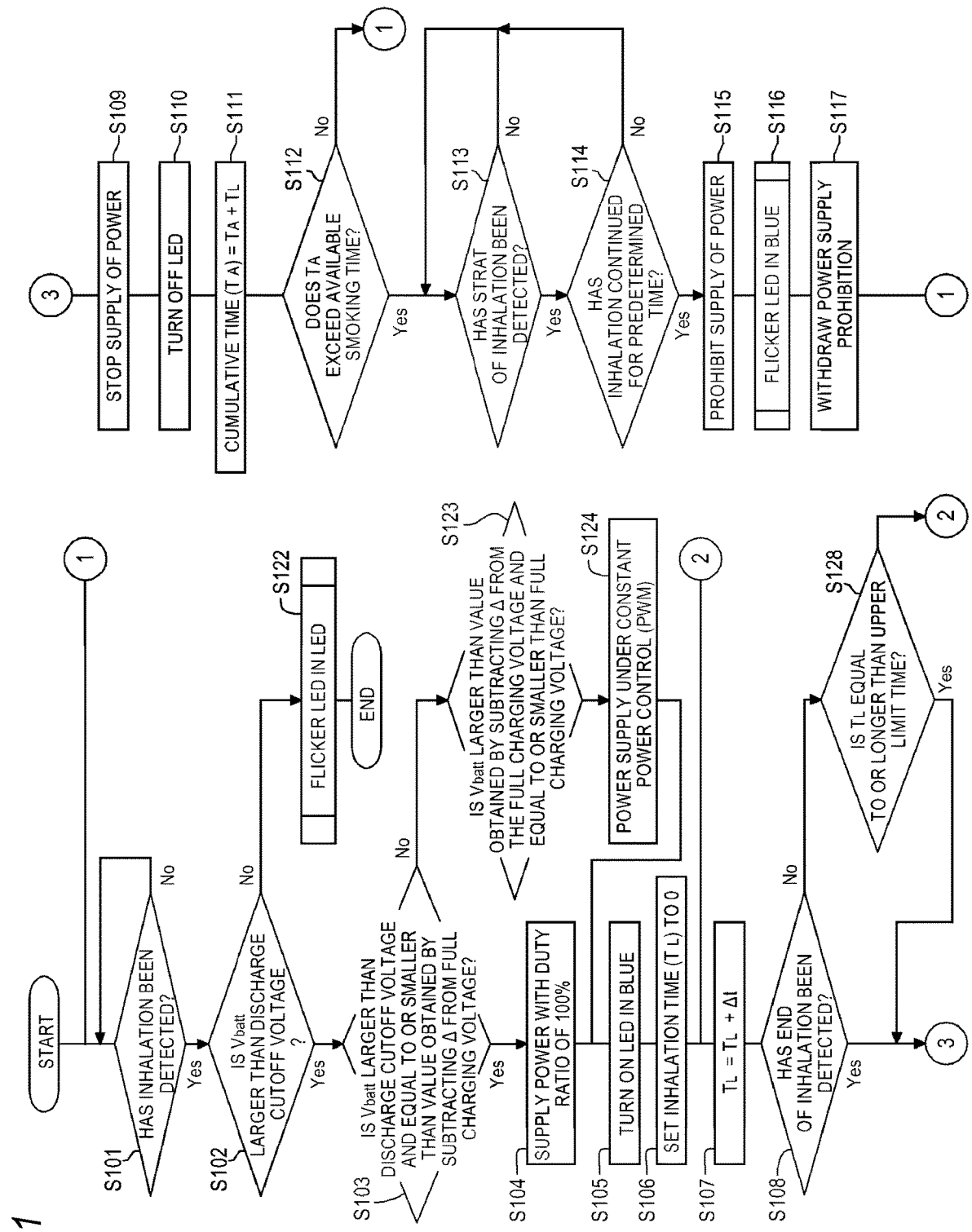
FIG. 11 is a flow chart illustrating a specific operation example of the inhalation component generating device.

The inhalation component generating device of the present embodiment may be a device which operates the light emitting unit 40 (see FIG. 1 and so on) as follows. However, as described above, it also is possible to give information to the user by a notifying means such as sound or vibration, instead of light emission. FIG. 11 is a flow chart illustrating a specific operation example of the inhalation component generating device 100.

First, in STEP S101, the control circuit 50 (see FIG. 3) detects whether inhalation has started. In the case where start of inhalation has not been detected, the control circuit repeats STEP S101; whereas in the case where start of inhalation has been detected, the control circuit proceeds to STEP S102.

Next, in STEP S102, the control circuit acquires the power-supply voltage value $V_{batt}$ of the power supply 10, and determines whether the acquired value is larger than the discharge cutoff voltage value (for example, 3.2 V) of the power supply 10. Since the case where the power-supply voltage value $V_{batt}$ is equal to or smaller than the discharge cutoff voltage value means the case where the residual amount of the power supply is not sufficient, in STEP S122, the control circuit controls the light emitting unit 40 such that the light emitting unit emits light in a predetermined mode. Specifically, for example, the control circuit may control the light emitting unit such that the light emitting unit blinks red.

In the case where it is determined in STEP S102 that the residual amount is sufficient since the power-supply voltage value $V_{batt}$ is larger than the discharge cutoff voltage value and, subsequently, in STEP S103, the control circuit determines whether the power-supply voltage value $V_{batt}$ is larger than the discharge cutoff voltage, and is equal to or smaller than the value obtained by subtracting A from the full charging voltage, or not. Also, Δ is a positive value. According to whether the power-supply voltage value $V_{batt}$ is in this range, whether to perform power supply with the duty ratio of 100% is switched as will be described below. In the case where the power-supply voltage value is in the corresponding range, in STEP S104, power supply with the duty ratio of 100% is performed. Although not limited, as an example, the light emitting unit 40 may be controlled so as to be turned on in blue (STEP S105).

Meanwhile, in the case where it is determined in STEP S103 that the power-supply voltage value $V_{batt}$ is not in the above-mentioned range, subsequently, in STEP S123, the control circuit determines whether the power-supply voltage value $V_{batt}$ is larger than the value obtained by subtracting A from the full charging voltage, and is equal to or smaller than the full charging voltage, or not. If the power-supply voltage value is in this range, in STEP S124, the control circuit supplies power using PWM control, thereby realizing constant power control.

In the present embodiment, in STEP S106, inhalation time $T_L$ is reset to "0", and thereafter, in STEP S107, Δt is added to the inhalation time $T_L$, whereby the inhalation time is updated.

Next, in STEP S108, the control circuit determines whether the end of the inhalation has been detected, and in the case where the end of the inhalation has been detected, the control circuit proceeds to STEP S109, and stops supply of power to the load. Meanwhile, even though the end of the inhalation has not been detected, if it is determined in STEP S128 that the inhalation time $T_L$ is equal to or longer than a predetermined upper limit time, the control circuit proceeds to STEP S109, and stops supply of power to the load. Then, in STEP S110, the control circuit turns off the light emitting unit 40.

In STEP S111, the cumulative time $T_A$ is updated. In other words, to the cumulative time $T_A$ until that moment, the current inhalation time $T_L$ is added, whereby the cumulative time $T_A$ is updated. Next, in STEP S112, the control circuit determines whether the cumulative time $T_A$ exceeds a predetermined available inhalation time (for example, 120 sec). In the case where the cumulative time does not exceed the available inhalation time, the control circuit determines that continuous use is possible, and returns to the sequence from STEP S101. Meanwhile, in the case where the cumulative time $T_A$ exceeds the available inhalation time, the control circuit estimates that the flavor source in the flavor unit 130 or the aerosol source in the reservoir 123 is insufficient or exhausted, and stops supply of power to the load in STEP S115 to be described below.

Meanwhile, in the case where the cumulative time exceeds the available inhalation time, the control circuit detects whether inhalation has started, in STEP S113, and determines whether the inhalation has continued for a predetermined time (for example, 1.0 sec), in STEP S114, and if it is determined that the inhalation has continued for the predetermined time or more, in STEP S115, the control circuit prohibits supply of power to the load. In this case, in STEP S116, in order to inform the above-mentioned power supply prohibition state, the control circuit controls the light emitting unit such that the light emitting unit emits light in a predetermined mode (for example, it blinks blue), and after a predetermined time passes, in STEP S117, the control circuit withdraws the power supply prohibition state. However, instead of elapse of the predetermined time, exchange of the flavor unit 130 or the cartridge unit 120 with a new one, or refilling of the flavor source or the aerosol source may be used as a condition for withdrawing the power supply prohibition state in STEP S117.

According to the series of operations described above, according to the residual amount of the power supply, the operation mode of the load is appropriately changed, and the user can grasp the current operation state of the inhalation component generating device due to the light emitting unit 40.

(a3) Operation Control based on Temperature of Power Supply

Figure 12:
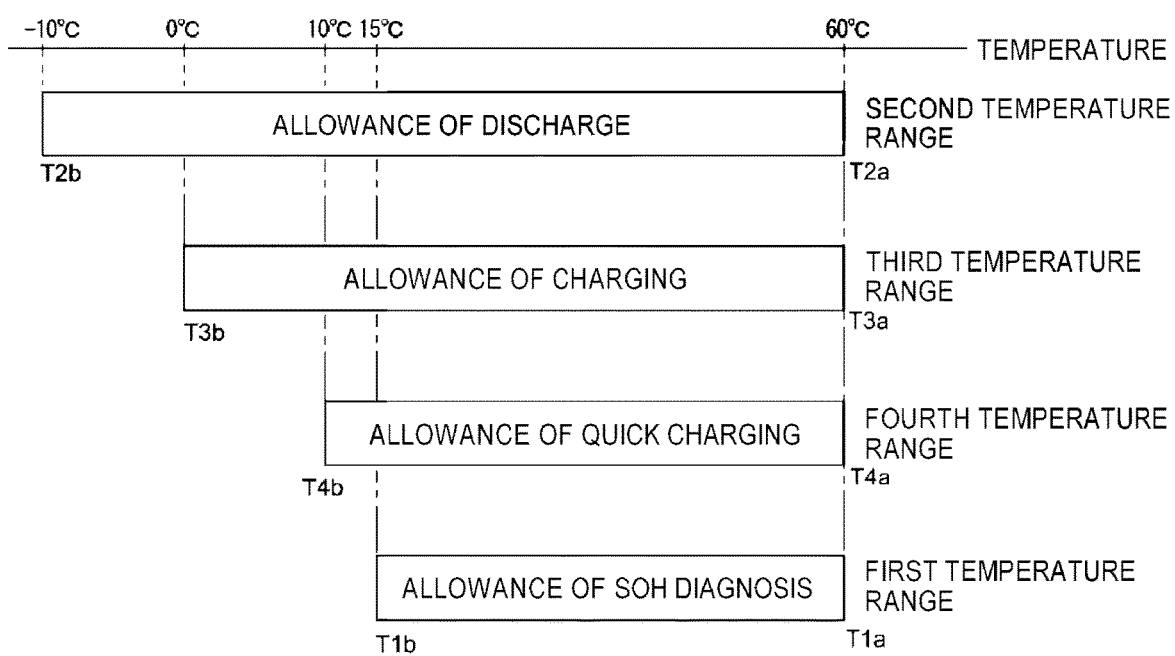
FIG. 12 is a view illustrating some temperature ranges for power supply temperature and operation control corresponding thereto.

The inhalation component generating device 100 of the present embodiment may be configured to determine whether power supply temperature $T_{batt}$ is in a predetermined temperature range, and determine to or not to perform a predetermined operation on the basis of the determination result. In FIG. 12, specific examples of temperature ranges are shown. In this example, a first temperature range to a fourth temperature range are set. However, not all of the four, only one, two, or three of them may be set.

The first temperature range is a temperature range related to allowance of diagnosis using SOH (State of health) representing the healthy state of the power supply, and has an upper limit temperature T1a and a lower limit temperature T1b. The specific numeric values of the upper limit temperature and the lower limit temperature can be appropriately set. Also, the unit of SOH may be %. In this case, on the assumption that the SOH of a new device is 100(%), the SOH when a device has deteriorated to such a state that charge and discharge are difficult may be set to 0(%). Also, as another example, as the SOH, a value which is obtained by dividing the current full charge capacity by the full charge capacity of a new device may be used.

The upper limit temperature T1a is not limited to, and for example, in consideration of the temperature at which there is a possibility that the structures and/or compositions of the electrodes and the electrolytic solution of the power supply might change (or the temperature at which change becomes remarkable), the temperature at which there is a possibility that cracked gas might be generated (or the temperature at which generation becomes remarkable), or the like, the upper limit temperature may be set to be lower than or equal to the corresponding temperature. If the SOH is acquired at a temperature equal to or higher than the upper limit temperature T1a, since the influence of the temperature is strong, it is difficult to obtain an adequate deterioration diagnosis result. As an example, the temperature T1a may be 60° C. If the temperature range is set as described above, in a range in which change of the structure of the power supply and the like do not occur and generation of cracked gas is suppressed, deterioration diagnosis can be performed. Therefore, it is possible to obtain an adequate deterioration diagnosis result.

For example, in consideration of the temperature at which there is a possibility that a decrease in the output attributable to low temperature might become predominate as compared to a decrease attributable to SOH (or the temperature at which it becomes remarkable), the lower limit temperature T1b may be set to be higher or equal to the corresponding temperature. The temperature T1b is, for example, 15° C. In general, to acquire SOH, an index indicating the deterioration of the capacity of the power supply 10 such as a decrease in the output is used. Therefore, in a temperature range in which SOH is not the only cause of the decrease in the output, it is difficult to obtain an adequate deterioration diagnosis result. In other words, if deterioration diagnosis is allowed only in the case where the temperature of the power supply is in the first temperature range which is determined from the upper limit temperature T1a and the lower limit temperature T1b, it is possible to minimize the influence of the temperature of the power supply on the deterioration diagnosis result. Therefore, it becomes possible to obtain an adequate deterioration diagnosis result.

The second temperature range is a temperature range relates to allowance of discharge of the power supply, and has an upper limit temperature T2a and a lower limit temperature T2b. The specific numeric values of the upper limit temperature and the lower limit temperature can be appropriately set. For example, the upper limit temperature T2a may be set on the basis of the same reference as that for the upper limit temperature T1a of the first temperature range. As an example, the temperature T2a is 60° C. Also, as another example, the upper limit temperature T2a may be different from the upper limit temperature T1a. For example, in consideration of the temperature at which there is a possibility that the internal resistance might excessively increase due to coagulation of the electrolytic solution or ionic liquid of the power supply (or the temperature at which the increase in the internal resistance becomes remarkable), the lower limit temperature T2b may be set to be higher or equal to the corresponding temperature. The temperature T2b may be, for example, −10° C. Since the second temperature range which is determined from the upper limit temperature T2a and the lower limit temperature T2b is a range in which the structures and/or compositions of the electrodes and the electrolytic solution of the power supply do not change, and coagulation of the electrolytic solution or ionic liquid of the power supply does not occur, it is possible to improve the safety of the power supply related to discharge, and the life of the power supply.

The third temperature range is a temperature range related to allowance of charging of the power supply, and has an upper limit temperature T3a and a lower limit temperature T3b. Similarly to the above-mentioned ranges, the specific numeric values of the upper limit temperature and the lower limit temperature can be appropriately set.

Although not limited, for example, the upper limit temperature T3a may be set on the basis of the same reference as that for the upper limit temperature T1a of the first temperature range. As an example, the upper limit temperature T3a is 60° C. Also, as another example, the upper limit temperature T3a may be different from the upper limit temperature T1a. For example, in the case where the power supply is a lithium-ion secondary battery, there is a possibility that if voltage is applied at low temperature, metallic lithium might be deposited on the surface of the negative electrode. In consideration of the temperature at which there is a possibility that this so-called electrocrystallization phenomenon might occur (or the temperature at which electrocrystallization becomes remarkable), the lower limit temperature T3b may be set to be higher than or equal to the corresponding temperature. The lower limit temperature T3b is, for example, 0° C. Since the third temperature range which is determined from the upper limit temperature T3a and the lower limit temperature T3b is a range in which the structures and/or compositions of the electrodes and the electrolytic solution of the power supply do not change, and electrocrystallization does not occur, it is possible to improve the safety of the power supply related to charging, and the life of the power supply.

The fourth temperature range is a temperature range related to allowance of quick charging, and has an upper limit temperature T4a and a lower limit temperature T4b. Similarly to the above-mentioned ranges, the specific numeric values of the upper limit temperature and the lower limit temperature can be appropriately set. Also, in this specification, quick charging is charging which is performed at a higher rate as compared to charging which is allowed in the third temperature range. As an example, quick charging may be performed at a higher rate which is two or more times that for charging. As an example, the rate of quick charging may be 2 C, and the rate of charging may be 1 C.

Although not limited, for example, the upper limit temperature T4$a$ may be set on the basis of the same reference as that for the upper limit temperature T1$a$ of the first temperature range. As an example, the upper limit temperature T4$a$ is 60° C. Also, as another example, the upper limit temperature T4$a$ may be different from the upper limit temperature T1$a$. For example, in consideration of the temperature at which deterioration of the power supply is promoted if charging is performed at a high rate, the lower limit temperature T4$b$ may be set to be higher than or equal to the corresponding temperature. The temperature T4$b$ is, for example, 10° C. Since the fourth temperature range which is determined from the upper limit temperature T4$a$ and the lower limit temperature T4$b$ is a range in which the structures and/or compositions of the electrodes and the electrolytic solution of the power supply do not change, and deterioration of the power supply is not promoted. Therefore, it is possible to improve the safety of the power supply related to quick charging, and the life of the power supply.

The first to fourth temperature ranges have been described above, and the individual temperature ranges may have the following relations.

(1) With respect to the first temperature range, its lower limit temperature T1$b$ may be set to be higher than the lower limit temperature T2$b$ of the second temperature range. Further, the lower limit temperature T1$b$ may be set to be higher than the lower limit temperatures T2$b$ to T4$b$ of the second to fourth temperature ranges. The upper limit temperature T1$a$ may be set to be the same as or substantially the same as the upper limit temperatures T2$a$ to T4$a$ of the other temperature ranges (which means that the upper limit temperature T1$a$ is in a numeric value range between values obtained by increasing and decreasing each comparison object value by 10%, and this is the same for this specification). Alternatively, the upper limit temperature T1$a$ may be equal to or higher than the upper limit temperature T2$a$ of the second temperature range, or may be equal to or higher than the upper limit temperature T3$a$ of the third temperature range, or may be equal to or higher than the upper limit temperature T4$a$ of the fourth temperature range.

(2) With respect to the second temperature range, the second temperature range may be set to be wider than the first temperature range and include the first temperature range (the case where one range is referred to as including another range includes the case where their upper limit temperatures are the same, or their lower limit temperatures are the same, and this is the same for this specification). In an embodiment of the present invention, the second temperature range may be set to be wider than the temperature ranges in which the other functions are allowed (in the example of FIG. 12, for example, the first, third, and fourth temperature ranges).

(3) With respect to the third temperature range, the third temperature range may be set to be wider than the first temperature range and include the first temperature range. Also, the third temperature range may be set to be wider than the fourth temperature range and include the fourth temperature range.

(4) With respect to the fourth temperature range, the fourth temperature range may be set to be wider than the first temperature range and include the first temperature range. In an embodiment of the present invention, the first temperature range may be set to be narrower than the temperature ranges in which the other functions are allowed (in the example of FIG. 12, for example, the second to fourth temperature ranges).

By the way, in general, SOH diagnosis is performed on the basis of an electric parameter of the power supply during discharge or during charging. As examples of the electric parameter, the value of current which the power supply releases during discharge, the voltage value which the power supply outputs during discharge, the current value with which the power supply is charged during charging, the voltage value which is applied to the power supply during charging, and so on may be used. If the first temperature range is set as described above, each power supply temperature belonging to the first temperature range necessarily belongs to the second to fourth temperature ranges. Therefore, in the state where SOH diagnosis is allowed, at least one of discharge, charging, and quick charging is allowed at the same time. Therefore, it is possible to acquire the electric parameter necessary for SOH diagnosis by any one of discharge, charging, and quick charging. Therefore, in the state where SOH diagnosis is allowed, it is possible to perform SOH diagnosis without any problems. Therefore, the effectiveness of SOH diagnosis improves.

Also, the electric parameter which is used in SOH diagnosis is influenced not only by deterioration of the power supply but also by the power supply temperature. Therefore, in order to secure the accuracy of SOH diagnosis, it is preferable to perform SOH diagnosis only in the case where the power supply temperature belongs to a temperature range in which the power supply temperature exerts little influence to the electric parameter which is used in SOH diagnosis.

As the result of earnest examination of the inventors of this application, it became evident that an appropriate temperature range for SOH diagnosis is narrower than a temperature range in which charging and discharge are possible without promoting deterioration of the power supply. Also, it became evident that particularly, during low temperature, the influence which the power supply temperature exerts on the electric parameter which is used in SOH diagnosis becomes predominate.

If the first temperature range is set as described above, power supply temperatures belonging to the second to fourth temperature ranges do not necessarily belong to the first temperature range. In other words, this means that there is a temperature range in which even though charging and discharge are allowed, SOH diagnosis is not allowed. If the individual temperature ranges are set as described above, SOH diagnosis is performed only in a proper temperature range. Therefore, it is possible to improve the accuracy of SOH diagnosis. Particularly, in the temperature range lower than 15° C., although charging and discharge of the power supply are allowed in order to suppress deterioration of the power supply, SOH diagnosis is not allowed in order to secure the accuracy of SOH diagnosis. This is preferable as an embodiment of the present invention.

Also, with respect to charging and discharge, in general, the influence of discharge on deterioration of the power supply is less. The difference in the influence on deterioration of the power supply between charging and discharge becomes more remarkable as the power supply temperature lowers. If the second temperature range is set as described above, it is possible to maximize the opportunity for charging and discharge while suppressing deterioration of the power supply.

Also, with respect to charging and quick charging, in general, the influence of charging on deterioration of the power supply is less. The difference in the influence on deterioration of the power supply between charging and quick charging becomes more remarkable as the power supply temperature lowers. If at least one of the third temperature range and the fourth temperature range is set as described above, it is possible to maximize the opportunity for charging and quick charging while suppressing deterioration of the power supply.

Like this, if the first temperature range is appropriately set, the accuracy of SOH diagnosis improves, and it is possible to use the power supply 10 for a longer time while securing safety. Therefore, energy saving effect is obtained.

Also, if the individual temperature ranges are appropriately set, deterioration of the power supply 10 is suppressed. Therefore, the life of the power supply 10 lengthens, and energy saving effect is obtained.

(a4) Deterioration Diagnosis Function

Figure 13:
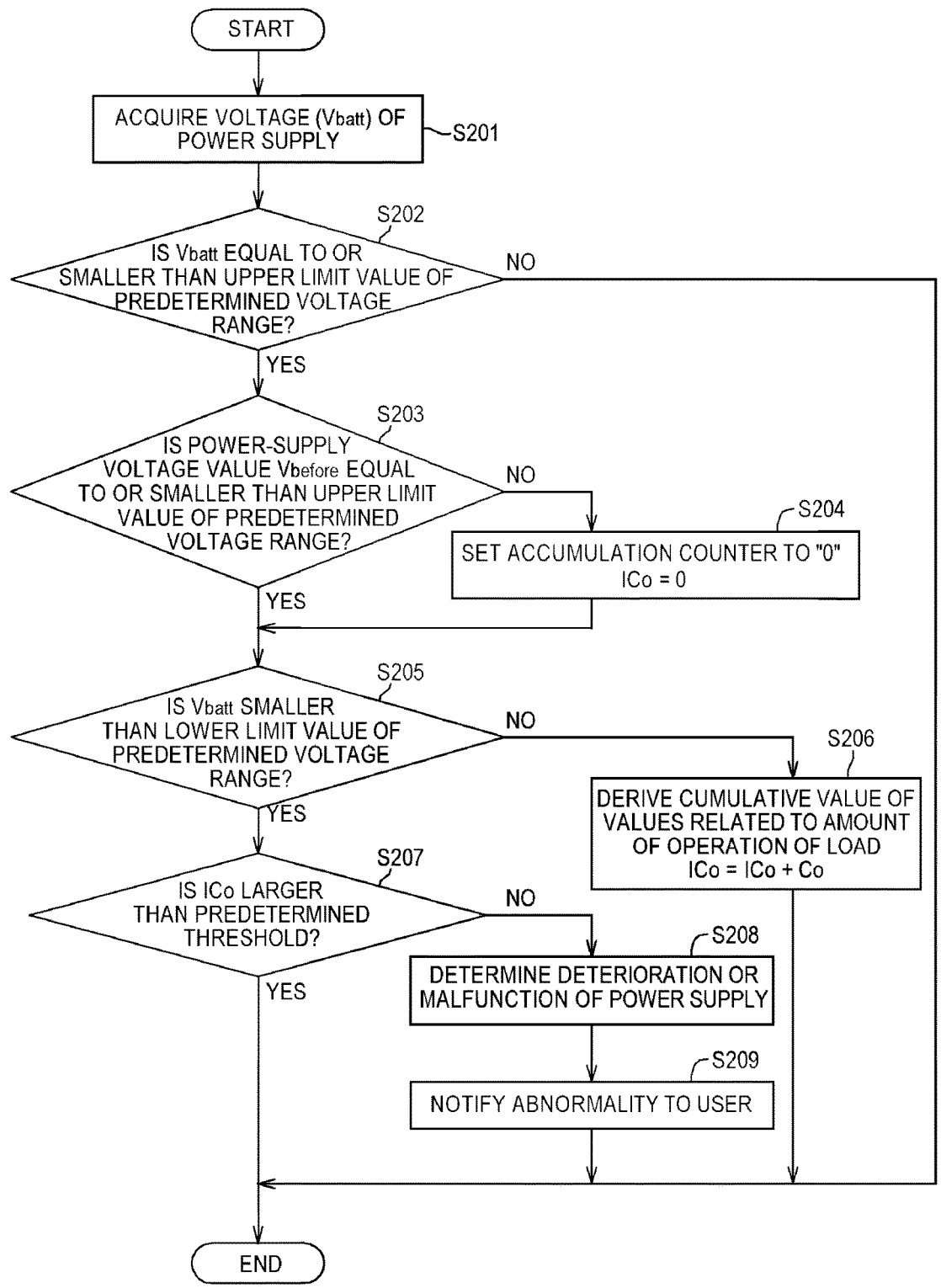
FIG. 13 is a flow chart illustrating an example of deterioration diagnosis.

FIG. 13 is a flow chart illustrating an example of deterioration diagnosis or malfunction diagnosis. In STEP S201, first, measuring of the power-supply voltage value $V_{batt}$ is performed. The power-supply voltage value $V_{batt}$ can be acquired by the voltage sensor. However, it should be noted that this flow chart is performed by the control circuit 50 in response to detecting start of inhalation (see FIG. 3). In other words, in response to the detection of the generation request of the inhalation component, the determination whether the power supply temperature $T_{batt}$ is in the first temperature range is performed, and the deterioration diagnosis is performed.

As an example, the power-supply voltage value $V_{batt}$ may be open circuit voltage (OCV) which can be acquired without electrically connecting the power supply 10 and the load 125. As another example, the power-supply voltage value $V_{batt}$ may be closed circuit voltage (CCV) which can be acquired by electrically connecting the power supply 10 and the load 125. As another example, as the power-supply voltage value $V_{batt}$, both of the open circuit voltage and the closed circuit voltage may be used. In some cases, in order to eliminate the influence of voltage drop attributable to the electric connection of the load and change of the internal resistance or the temperature attributable to discharge, it is preferable to use the open circuit voltage (OCV) rather than the closed circuit voltage (CCV). From the closed circuit voltage (CCV), the open circuit voltage (OCV) may be estimated.

Specifically, the acquisition timing of the power-supply voltage value $V_{batt}$ may be a timing when discharge is being performed to supply power to the load, or may be a timing immediately before discharge, or may be a timing immediately after discharge. The timing immediately before discharge may be, for example, a period before start of discharge, for example, a period from 5 msec to 10 msec before discharge until discharge start time. The timing immediately after discharge may be, for example, a period from the end of discharge until, for example, 5 msec to 10 msec passes.

Also, in the flow of FIG. 13, acquisition of the power-supply voltage value $V_{batt}$ in the course of charging is not performed; however, in the case where it is required to acquire the power-supply voltage value $V_{batt}$ in the course of charging, similarly, not only in the course of charging, but also at the timing immediately before charging, or at the timing immediately after charging, the power-supply voltage value $V_{batt}$ may be acquired. The timing immediately before charging may be, for example, a period from a time before start of charging, for example, 5 msec to 10 msec before start of charging until the charging start time. The timing immediately after charging may be, for example, a period from the end of charging until, for example, 5 msec to 10 msec passes.

Next, in STEP S202, whether the acquired power-supply voltage value $V_{batt}$ is equal to or smaller than the upper limit value of a predetermined voltage range, or not is determined. In the case where the power-supply voltage value is larger than the upper limit value, the process is finished without estimating or detecting deterioration and malfunction of the power supply. As another example, in the case where the power-supply voltage value is larger than the upper limit value, the process may return to STEP S201.

Meanwhile, in the case where the power-supply voltage value $V_{batt}$ is equal to or smaller than the predetermined upper limit value, subsequently, in STEP S203, whether the power-supply voltage value acquired during the previous inhaling action is equal to or smaller than the upper limit value of the predetermined voltage range or not is determined. In the case where the power-supply voltage value $V_{before}$ acquired during the previous inhaling action is larger than the upper limit value of the predetermined voltage range, it is determined that the power-supply voltage value has become equal to or smaller than the upper limit value of the predetermined voltage range for the first time by the latest inhaling action. Next, in STEP S204, an accumulation counter ($I_{Co}$) which counts the cumulative value of values related with the amount of operation of the load 125 is set to "0". The case where the result of STEP S203 is "No" means that in the period from the previous inhaling action to the current inhaling action, the power supply has been charged.

In the case where the result of STEP S203 is "Yes", or after the accumulation counter is reset in STEP S204, subsequently, in STEP S205, whether the power-supply voltage value $V_{batt}$ is smaller than the lower limit value of the predetermined voltage range is determined. In the case where the power-supply voltage value $V_{batt}$ is equal to or larger than the lower limit value, in STEP S206, the sum of values related to the amount of operation of the load is derived by "ICo=ICo+Co". Co is the value related to the amount of operation of the load during the current inhaling action. ICo is the cumulative value of values related to the amount of operation of the load. Thereafter, the process is finished without estimating or detecting deterioration or malfunction of the power supply.

In the case where it is determined in STEP S205 that the power-supply voltage value $V_{batt}$ is smaller than the lower limit value of the predetermined voltage range, subsequently, in STEP S207, whether the value related to the amount of operation of the load having operated while the power-supply voltage value $V_{batt}$ has been in the predetermined voltage range, i.e. the cumulative value ICo is larger than a predetermined threshold is determined. In the case where the cumulative value ICo is larger than the predetermined threshold, it is determined that the power supply is normal, and the process of the diagnosis function is finished.

In the case where the cumulative value ICo is equal to or smaller than the predetermined threshold, deterioration or malfunction of the power supply 10 is determined (STEP S208), and the abnormality is notified the user via the light emitting unit 40 (STEP S209). If deterioration or malfunction of the power supply is determined, according to the needs, control may be performed to make supply of power to the load 125 impossible.

The deterioration diagnosis function is not limited to the above-described embodiment, and various known methods can be used. As an example, in the case of discharging the power supply 10 in a constant current mode or in a constant power mode, if the power-supply voltage significantly lowers, deterioration of the power supply 10 may be determined. Also, as another example, in the case of charging the power supply 10, if the power-supply voltage rises early, deterioration of the power supply 10 may be determined. Also, as another example, in the case of charging the power supply 10, if the power-supply voltage lowers, malfunction of the power supply 10 may be determined. Also, as another example, in the case of charging or discharging the power supply 10, if the rate of temperature increase of the power supply 10 is high, deterioration of the power supply 10 may be determined. Also, as another example, if any one of the cumulative charging amount, cumulative charging time, cumulative discharge amount, and cumulative discharge time of the power supply 10 exceeds a threshold, deterioration of the power supply 10 may be determined.

(a5) Example of Operation Control based on Temperature of Power Supply

Figure 14:
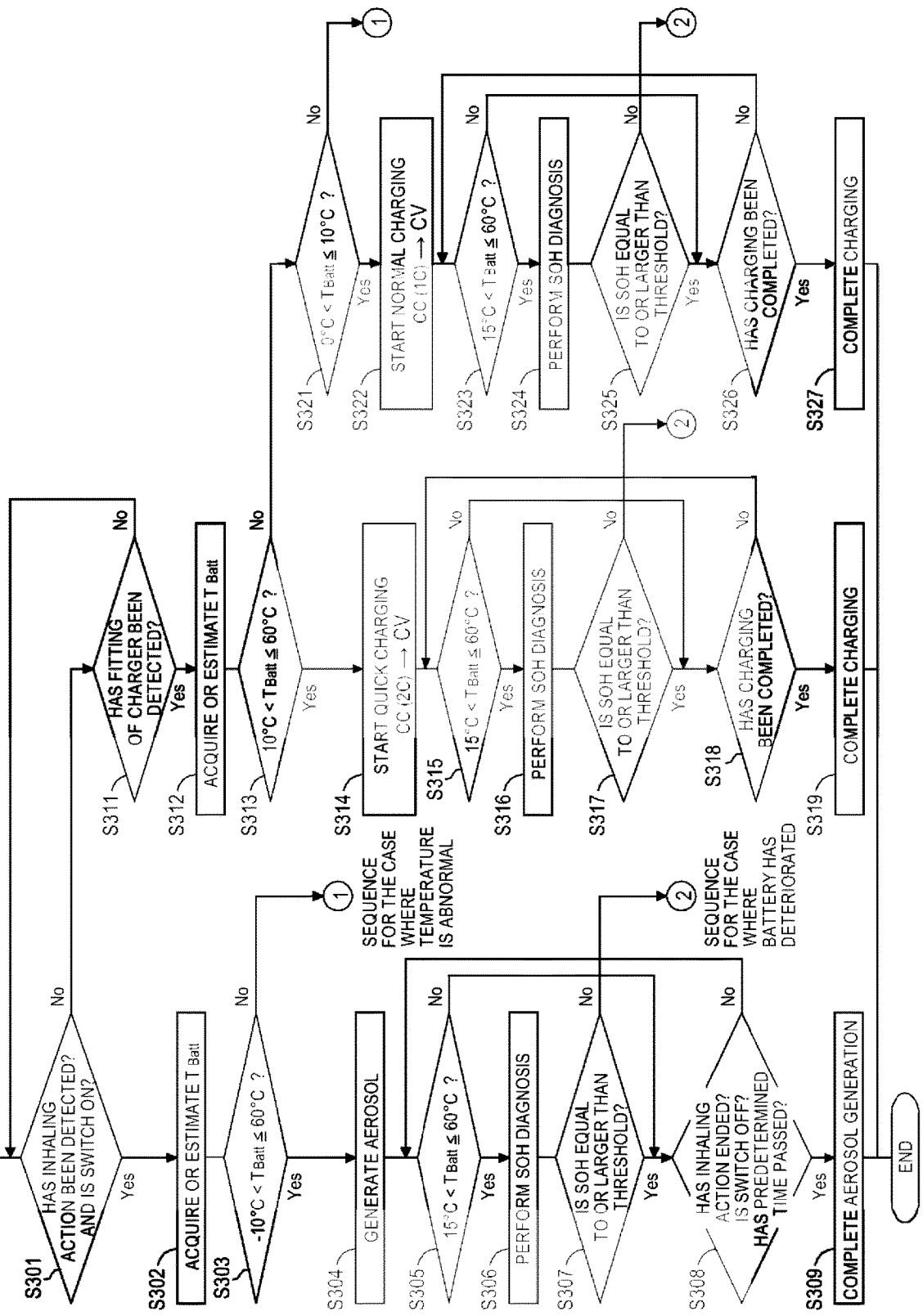
FIG. 14 is a flow chart illustrating another specific operation example of the inhalation component generating device.

Now, an example of the operation of the inhalation component generating device 100 of the present embodiment will be described with reference to the flow chart of FIG. 14. This flow chart shows an example of operation control based on the power supply temperature $T_{batt}$.

First, in STEP S301, the inhalation component generating device 100 determines whether an inhaling action has been detected, and whether a switch 30 (see FIG. 1) is on. As described above, the detection of an inhaling action may be detection based on the output of the inhalation sensor 20.

In the case where the result of STEP S301 is "No", the inhalation component generating device performs STEP S311 and the subsequent steps. This will be described below. Meanwhile, in the case where the result of STEP S301 is "Yes", a user's aerosol generation request is detected. Next, in STEP S302, the inhalation component generating device calculates the power supply temperature $T_{batt}$. As described above, the calculation of the power supply temperature $T_{batt}$ may be a process of detecting the temperature of the power supply 10 by a temperature sensor and obtaining the power supply temperature on the basis of the output of the temperature sensor, or may be a process of estimating the power supply temperature on the basis of a value related to the temperature of the power supply, or may be a process of detecting the temperature of an object other than the power supply by a temperature sensor and estimating the power supply temperature on the basis of the output of the temperature sensor. The calculation of the power supply temperature is not limited to specific means, and any means can be used as long as it can acquire or estimate the current temperature of the power supply.

After STEP S302, in STEP S303, the inhalation component generating device 100 determines whether the power supply temperature $T_{batt}$ is in the second temperature range. As an example, the inhalation component generating device determines whether the power 15 supply temperature is included in the range of $-10°$ C.$<T_{batt} \leq 60°$ C.

In the case where $T_{batt}$ is not in the range (the case where the result of STEP S302 is "No"), the inhalation component generating device performs a sequence for the case where the temperature is abnormal (STEPS S381 and S382). This will be described below.

Meanwhile, in the case where $T_{batt}$ is in the range (the case where the result of STEP S302 is "Yes"), subsequently, in STEP S304, the inhalation component generating device 100 performs aerosol generation. Aerosol generation is performed by performing supply of power to the load 125. Control on supply of power is not limited to specific control, and a variety of control including the above-mentioned method and methods known in the art can be used.

Next, in STEP S305, the inhalation component generating device 100 determines whether the power supply temperature $T_{batt}$ is in the first temperature range. As an example, the inhalation component generating device determines whether the power supply temperature is included in the range of 15° C.$<T_{batt} \leq 60°$ C.

In the case where the power supply temperature $T_{batt}$ is in the above-mentioned temperature range (the case where the result of STEP S305 is "Yes"), in STEPS S306 and S307, the inhalation component generating device 100 performs SOH diagnosis and so on. Specifically, the inhalation component generating device performs SOH diagnosis in STEP S306, and determines whether the SOH is equal to or larger than a predetermined threshold or not, in STEP S307. However, deterioration diagnosis also is not limited to specific control, and a variety of control including the above-mentioned method and methods known in the art can be used.

In the case where the SOH is equal to or larger than the predetermined threshold (the case where the result of STEP S307 is "Yes"), since it is determined that the power supply 10 has not deteriorated, subsequently, STEPS S308 and S309 to be described below are performed.

Figure 16:
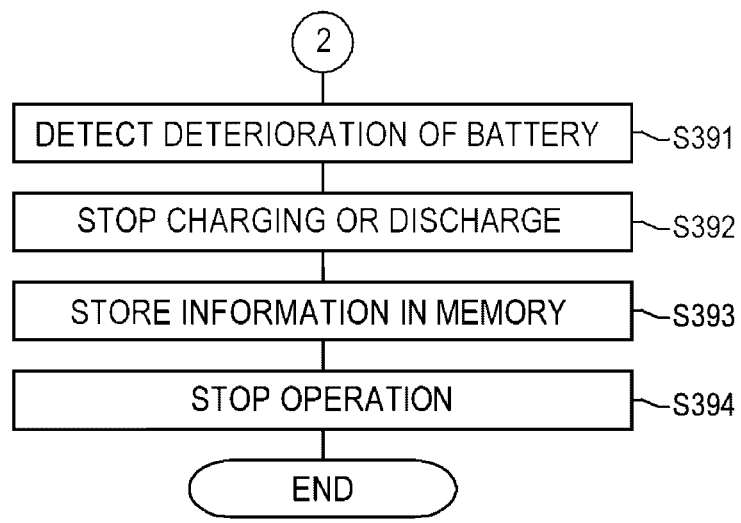
FIG. 16 is a flow chart illustrating a sequence which is performed during battery deterioration.

Meanwhile, in the case where the SOH is smaller than the predetermined threshold (the case where the result of STEP S307 is "No"), since it is determined that the power supply 10 has deteriorated, the inhalation component generating device performs a sequence for the case where the battery has deteriorated (STEPS S391 to S394, see FIG. 16). This will be described below.

In the case where it is determined in STEP S305 that the power supply temperature $T_{batt}$ is not in the above-mentioned temperature range, STEPS S306 and S307 are skipped, so SOH diagnosis is not performed. In other words, in the present embodiment, only in the case where the power supply temperature Tat is in the first temperature range, SOH diagnosis is performed. Although not limited, the inhalation component generating device may be configured such that in the case where the power supply temperature is not in the range, in order to inform that it is impossible to perform diagnosis, a predetermined notification (such as light emission of the light emitting unit 40) is issued.

Referring to FIG. 14 again, subsequently, in STEP S308, the inhalation component generating device 100 determines whether the inhaling action has ended, whether the switch is off, and whether a predetermined time has passed. In the case where the result of STEP S308 is "No" (i.e. the case where the inhaling action has not ended, and the switch is on, and the predetermined time has not passed), the inhalation component generating device returns to STEP S305. Meanwhile, in the case where the result of STEP S308 is "Yes", in STEP S309, the inhalation component generating device completes aerosol generation. As another example, in the case where the result of STEP S308 is "No", the inhalation component generating device may return to STEP S306, not to STEP S305. In this case, since the flow speeds up, it is possible to increase the number of times of SOH diagnosis.

According to the series of steps described above, only in the case where the power supply temperature $T_{batt}$ is in the temperature range in which discharge is possible, supply of power is performed, and only in the case where the power supply temperature Tan is in the temperature range in which deterioration diagnosis is possible, deterioration diagnosis is performed. If SOH diagnosis is allowed only in a part of the temperature range in which discharge of the power supply 10 is allowed, SOH diagnosis is performed only in the temperature range in which the influence which is exerted by the power supply temperature is less. Therefore, it is possible to improve the accuracy of SOH diagnosis.

(Quick Charging)

Now, STEP S311 and the subsequent steps which are performed in the case where the result of STEP S301 is "No" will be described. First, in STEP S311, the inhalation component generating device 100 detects whether the charger has been fit. In the case where fitting of the charger has not detected, the inhalation component generating device returns to STEP S301.

In the case where fitting of the charger has been detected, in STEP S312, the inhalation component generating device 100 acquires or estimates the power supply temperature $T_{batt}$. The acquisition or estimation of the power supply temperature $T_{batt}$ can be performed in the same way as that in STEP S302.

Next, in STEP S313, the inhalation component generating device 100 determines whether the power supply temperature $T_{batt}$ is in the fourth temperature range. As an example, the inhalation component generating device determines whether the power supply temperature is included in the range of $10°$ C.$<T_{batt} \leq 60°$ C.

In the case where the power supply temperature $T_{batt}$ is in the range (the case where the result of STEP S313 is "Yes"), subsequently, in STEP S314, the inhalation component generating device 100 performs quick charging. Also, the charging rate for quick charging in the CC mode may be 2 C.

Meanwhile, in the case where the power supply temperature $T_{batt}$ is not in the range (the case where the result of STEP S313 is "No"), the inhalation component generating device 100 performs the sequence for normal charging, not for quick charging (the sequence from STEP S321 which will be described below).

If quick charging is started in STEP S314, subsequently, in STEP S315, the inhalation component generating device 100 determines whether the power supply 30 temperature $T_{batt}$ is in the first temperature range (for example, $15°$ C.$<T_{batt} \leq 60°$ C.).

In the case where the power supply temperature $T_{batt}$ is in the above-mentioned temperature range (the case where the result of STEP S313 is "Yes"), in STEPS S316 and S317, the inhalation component generating device 100 performs SOH diagnosis and so on. Specifically, the inhalation component generating device performs SOH diagnosis in STEP S316, and determines whether the SOH is equal to or larger than a predetermined threshold or not, in STEP S317. In the case where $T_{batt}$ is in the first range, STEPS S316 and S317 are skipped, so SOH diagnosis is not performed.

In the case where the SOH is equal to or larger than the predetermined threshold (the case where the result of STEP S317 is "Yes"), since it is determined that the power supply 10 has not deteriorated, subsequently, STEPS S318 and S319 to be described below are performed.

Meanwhile, in the case where the SOH is smaller than the predetermined threshold (the case where the result of STEP S317 is "No"), since it is determined that the power supply 10 has deteriorated, the inhalation component generating device performs a sequence for the case where the battery has deteriorated (STEPS S391 to S394, see FIG. 16).

Subsequently, in STEP S318, the inhalation component generating device 100 performs detection of a charging completion flag. In the case where the result of STEP S318 is "No" (i.e. the case where charging has not been completed), the inhalation component generating device returns to STEP S315. In the case where the result of STEP S318 is "Yes", in STEP S319, the inhalation component generating device completes charging. As another example, in the case where the result of STEP S318 is "No", the inhalation component generating device may return to STEP S316, not to STEP S315. In this case, since the flow speeds up, it is possible to increase the number of times of SOH diagnosis.

As described above, if SOH diagnosis is allowed only in a part of the temperature range in which quick charging of the power supply 10 is allowed, SOH diagnosis is performed only in the temperature range in which the influence which is exerted by the power supply temperature is less. Therefore, it is possible to improve the accuracy of SOH diagnosis.

(Normal Charging)

In the case where it is determined in STEP S313 described above that the power supply temperature $T_{batt}$ is not in the fourth temperature range (for example, $10°$ C.$<T_{batt} \leq 60°$ C.), in STEP S321, the inhalation component generating device 100 determines whether the power supply temperature is in the range of $0°$ C.$<T_{batt} \leq 10°$ C. (the inhalation component generating device determines whether the power supply temperature is in the third temperature range, on the basis of the combination of the content of STEP S313 and the content of STEP S321). In the case where Tan is not in the range (the case where the result of STEP S321 is "No"), the inhalation component generating device performs the sequence for the case where the temperature is abnormal (STEPS S381 and S382 to be described below in detail). In the case where the power supply temperature $T_{batt}$ is in the range (the case where the result of STEP S321 is "Yes"), subsequently, in STEP S322, the inhalation component generating device 100 performs normal charging. Also, the charging rate for normal charging in the CC mode may be 1 C.

If normal charging is started in STEP S322, subsequently, in STEP S323, the inhalation component generating device 100 determines whether the power supply temperature $T_{batt}$ is in the first temperature range (for example, $15°$ C.$<T_{batt} \leq 60°$ C.).

In the case where the power supply temperature $T_{batt}$ is in the above-mentioned range (the case where the result of STEP S323 is "Yes"), in STEPS S324 and S325, the inhalation component generating device 100 performs SOH diagnosis and so on.

Specifically, the inhalation component generating device performs SOH diagnosis in STEP S324, and determines whether the SOH is equal to or larger than a predetermined threshold or not, in STEP S325. In the case where the power supply temperature $T_{batt}$ is not in the first range (the case where the result of STEP S323 is "No"), STEPS S324 and S325 are skipped, so SOH diagnosis is not performed.

In the case where the SOH is equal to or larger than the predetermined threshold (the case where the result of STEP S325 is "Yes"), since it is determined that the power supply 10 has not deteriorated, subsequently, STEPS S326 and S327 to be described below are performed.

Meanwhile, in the case where the SOH is smaller than the predetermined threshold (the case where the result of STEP S325 is "No"), since it is determined that the power supply 10 has deteriorated, the inhalation component generating device performs a sequence for the case where the battery has deteriorated (STEPS S391 to S394, see FIG. 16).

Subsequently, in STEP S326, the inhalation component generating device 100 performs detection of a charging completion flag. In the case where the result of STEP S326 is "No" (i.e. the case where charging has not been completed), the inhalation component generating device returns to STEP S323. As another example, in the case where the result of STEP S326 is "No", the inhalation component generating device may return to STEP S324, not to STEP S323. In this case, since the flow speeds up, it is possible to increase the number of times of SOH diagnosis. In the case where the result of STEP S326 is "Yes", in STEP S327, the inhalation component generating device completes charging.

As described above, if SOH diagnosis is allowed only in a part of the temperature range in which charging of the power supply 10 is allowed, SOH diagnosis is performed only in the temperature range in which the influence which is exerted by the power supply temperature is less. Therefore, it is possible to improve the accuracy of SOH diagnosis.

(Sequence for the Case where Temperature is Abnormal)

Figure 15:
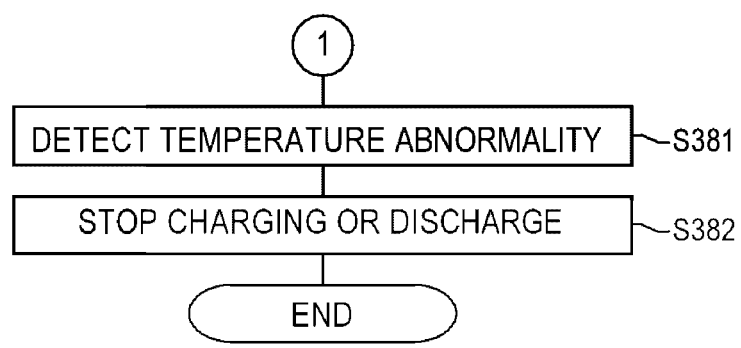
FIG. 15 is a flow chart illustrating a sequence which is performed when temperature is abnormal.

The sequence for the case where the temperature is abnormal may be, for example, the sequence as shown in FIG. 15 in which the inhalation component generating device 100 may first detect temperature abnormality in STEP S381, and subsequently perform stop of charging or stop of discharge in STEP S382. Also, under a condition such as a condition that a predetermined time should pass or the power supply temperature should return to the normal range, charging or discharge stopped in STEP S382 may be allowed again.

(Sequence for the Case where the Power Supply has Deteriorated)

The sequence for the case where the power supply has deteriorated may be, for example, the sequence as shown in FIG. 16. In this example, if the inhalation component generating device 100 first detects deterioration of the battery in STEP S391, subsequently, in STEP S392, the inhalation component generating device performs stop of charging or stop of discharge.

Subsequently, in STEP S393, the inhalation component generating device stores the detection time of the deterioration of the power supply and the condition under which the deterioration was detected, in a memory. Then, in STEP S394, the inhalation component generating device stops the series of operations. However, under a condition such as exchange of the power supply 10, the series of operations stopped in STEP S394 may be allowed again.

If comparing the sequence for the case where the temperature is abnormal and the sequence for the case where the power supply has deteriorated, it can be said that the condition for allowing charging or discharge stopped in STEP S382 again is more difficult to be satisfied than the condition for allowing the series of operations stopped in STEP S394 again is.

If comparing the sequence for the case where the temperature is abnormal and the sequence for the case where the power supply has deteriorated, charging or discharge stopped in STEP S382 is allowed again if the inhalation component generating device is left as it is. Meanwhile, it can be said that the series of operations stopped in STEP S394 may be allowed again if the inhalation component generating device 100 is left as it is.

As described above, if the first temperature range is appropriately set, the accuracy of SOH diagnosis improves, and it is possible to use the power supply 10 for a longer time while securing safety. Therefore, energy saving effect is obtained.

Also, if the individual temperature ranges are appropriately set, deterioration of the power supply 10 is suppressed.

Therefore, the life of the power supply 10 lengthens, and energy saving effect is obtained.

(b1) Detection of Connection of Charger or Others

With respect to charging control, detection of a connection of the charger, and so on, various methods can be appropriately used, and hereinafter, examples of them will be described in brief. The charging control unit 250 (see FIG. 8) has the function of detecting an electric connection between the electric circuit of the charger 200 and the electric circuit of the power supply unit 110. The method of detecting an electric connection between them is not particularly limited, and various methods can be used. For example, a connection of the power supply unit 110 may be detected by detecting the voltage difference between a pair of electric terminals 221t.

In an embodiment, it is preferable that when the charger 200 and the power supply unit 110 are connected, it should be possible to determine at least one of the type of the power supply unit 110 connected and the type of the power supply 10 connected. In order to realize this, for example, on the basis of a value related to the electric resistance value of the first resistor 150 (see FIG. 8), at least one of the type of the power supply unit 110 and the type of the power supply 10 provided in the power supply unit 110 may be determined. In other words, first resistors 150 having different electric resistance values may be provided in different types of power supply units 110, respectively, such that it is possible to determine the type of a power supply unit 110 or a power supply 10 connected. Also, a value related to the electric resistance value of a first resistor may be the electric resistance value of the first resistor 150, or may be the amount of voltage drop of the first resistor 150 (a potential difference), or may be the current value of the current passing through the first resistor 150.

(b2) Charging Control

Figure 17:
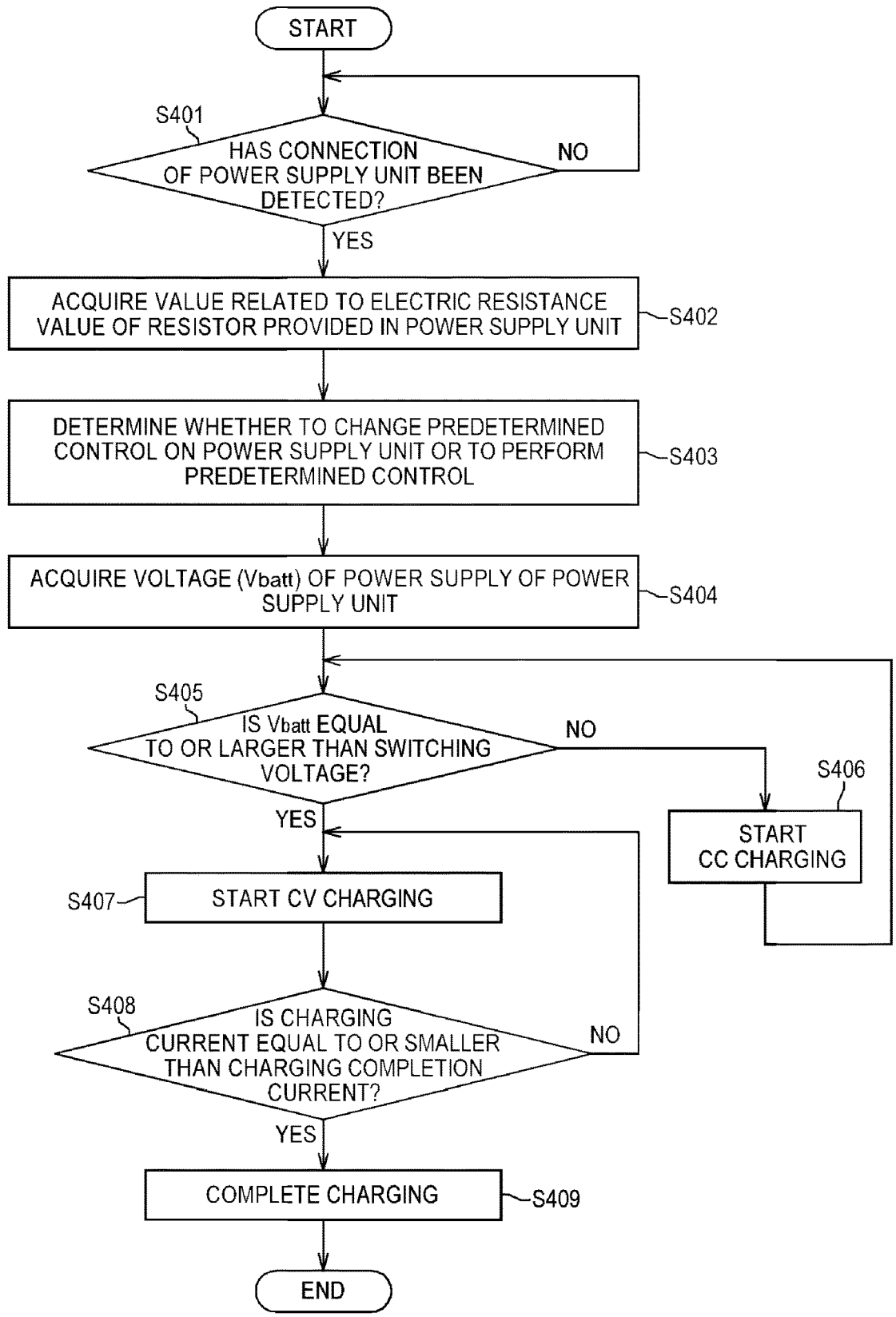
FIG. 17 is a flow chart illustrating an example of a charging operation.

Now, charging control will be described. Hereinafter, an example in which the charging control unit 250 of the charger 200 controls operations will be described; however, as described above, in the configuration in which the inhalation component generating device 100 has the function related to charging, the subject of control may be the control circuit 50 provided in the device. FIG. 17 is a flow chart illustrating an example of a control method which is performed by the charging control unit 250. First, in STEP S401, the charging control unit detects a connection of the power supply unit 110 with the charger 200.

After the connection is detected (in the case where the result of STEP S401 is "Yes"), subsequently, in STEP S402, the charging control unit acquires a value related to the electric resistance value of the first resistor 150. The charging control unit may acquire values which are measurement objects, a plurality of times, on the occasion of this measurement, and obtain a final value using the moving average, simple average, or weighted average of them on the basis of them.

Next, in STEP S403, the charging control unit determines whether it is necessary to change predetermined control or it is OK to perform the predetermined control, on the basis of the value related to the electric resistance value.

For example, in the case where the value related to the electric resistance value is out of a predetermined range, or in the case where a predetermined condition is not satisfied, the charging control unit may not perform charging of the power supply 10. Meanwhile, in the case where the value related to the electric resistance value is in the predetermined range, or in the case where the predetermined condition is satisfied, the charging control unit may perform charging. In other words, change of the predetermined control mentioned above include making change so as not perform the charging process. In this case, in the case where it is determined that the power supply unit is abnormal or the power supply unit is not genuine, since charging current is not transmitted, it is possible to suppress occurrence of an abnormity.

Also, besides, change of the predetermined control may be at least one of change of the current value for charging, change of the charging rate, and change of the charging time. As a specific example, in an embodiment, it is preferable to determine the type of the power supply unit 110 or the power supply 10 on the basis of the value related to the electric resistance value, such that it is possible to change the rate of charging current according to the determined type. In this case, for example, it becomes possible to perform charging control on a power supply 10 corresponding to quick charging with charging current with a high rate equal to or higher than 2 C, or perform normal charging control on a power supply 10 which does not correspond to quick charging, with charging current with a low rate equal to or lower than 1 C.

Next, in STEP S404, the charging control unit acquires the power-supply voltage value $V_{batt}$. Subsequently, in STEP S405, the charging control unit determines whether the acquired power-supply voltage value $V_{batt}$ is equal to or larger than a predetermined switching voltage or not. The switching voltage is a threshold for separating a constant current charging (CC charging) section and a constant voltage charging (CV charging) section, and although the specific numeric value of the switching voltage is not particularly limited, it may be, for example, in the range between 4.0 V and 4.1 V.

In the case where the power-supply voltage value $V_{batt}$ is smaller than the switching voltage (the case where the result of STEP S405 is "No"), constant current charging (CC charging) is performed (STEP S406). In the case where the power-supply voltage value is equal to or larger than the switching voltage (the case where the result of STEP S405 is "Yes"), constant voltage charging (CV charging) is performed (STEP S407). Also, in the constant voltage charging mode, as charging progresses, the power-supply voltage increases, and the difference between the power-supply voltage and the charging voltage decreases, so charging current decreases.

In the case where charging has started in the constant voltage charging mode, in STEP S408, the charging control unit determines whether the charging current is equal to or smaller than predetermined charging completion current. Also, the charging current can be acquired by the current sensor 230 provided in the charger 200. In the case where the charging current is larger than the predetermined charging completion current (the case where the result of STEP S408 is "No"), the charging control unit keeps charging in the constant voltage charging mode. In the case where the charging current is equal to or smaller than the predetermined charging completion current (the case where the result of STEP S408 is "Yes"), the charging control unit determines that the power supply 10 is fully charged, and stops charging (STEP S409).

Also, naturally, as the condition for stopping charging, besides the charging current, the time from start of charging in the constant current charging mode or start of charging in the constant voltage charging mode, the power-supply voltage value, the power supply temperature value, and so on may be used.

Although the embodiment of the present invention has been described above with reference to the drawings, the present invention can be appropriately modified without departing from the spirit of the present invention.

For example, in the flow chart of FIG. 14, basically, on the assumption of the process which is performed by a single control circuit, in STEP S313, first, whether quick charging is possible (the fourth temperature range) is determined, and in the case where quick charging is impossible, subsequently, in STEP S321, whether normal charging is possible (the third temperature range) is determined. However, the charger 200 may be configured to determine whether the power supply temperature is in the fourth temperature range, and perform quick charging in the case where the determination result is "Yes", and perform normal charging in the case where the determination result is "No".

(Additional Note)

This application discloses the following inventions, which are listed in the following in the form of numbered items. Also, reference symbols and specific numeric values are shown as references, but are not meant to limit the present invention at all.

1. An inhalation component generating device comprising: a power supply; a load that evaporates or atomizes an inhalation component source by power from the power supply; and a control circuit that performs control based on an output of a temperature sensor, wherein the control circuit performs: a process (a) of calculating power supply temperature based on the output of the temperature sensor; and a process (b1) of determining whether the power supply temperature is in a first temperature range, and performing deterioration diagnosis on the power supply only in a case where the power supply temperature is in the range.

According to this configuration, only in the case where the temperature of the power supply is in the temperature range in which it is possible to perform deterioration diagnosis, deterioration diagnosis is performed. Therefore, for example, the influence of low temperature or high temperature on diagnosis is suppressed. Therefore, it is possible to improve the accuracy of deterioration diagnosis.

2. The inhalation component generating device disclosed in Item 1 further comprising: a current sensor that outputs a charging/discharge current value of the power supply or a voltage sensor that outputs an output voltage value of the power supply, wherein the control circuit is configured to perform the deterioration diagnosis based on an output value of the current sensor or the voltage sensor at any one of a timing in a course of discharge of the power supply, a timing immediately before discharge, a timing immediately after discharge, a timing in a course of charging, a timing immediately before charging, and a timing immediately after charging.

As described above, the present invention may perform deterioration diagnosis in the course of discharge.

3. The inhalation component generating device disclosed in Item 2, wherein the control circuit is configured to perform a process (c1) of determining whether the power supply temperature is in a second temperature range in which discharge of the power supply is allowed, or whether the power supply temperature is in a third temperature range in which charging of the power supply is allowed, prior to the process (b1).

4. The inhalation component generating device disclosed in Item 3, wherein the control circuit is configured to perform the process (b1) only in a case where the determination in the process (c1) is positive.

5. The inhalation component generating device disclosed in Item 3, wherein the second temperature range or the third temperature range is wider than the first temperature range, and includes the first temperature range.

6. The inhalation component generating device disclosed in any one of Items 1 to 5, wherein an upper limit temperature of the first temperature range is lower than a temperature at which change of a structure or composition of an electrode of the power supply might occur.

7. The inhalation component generating device disclosed in any one of Items 3 to 6, wherein a lower limit temperature of the first temperature range is higher than a lower limit of the second temperature range, or is higher than a lower limit of the third temperature range.

8. The inhalation component generating device disclosed in Item 7, wherein the control circuit is configured to be able to further perform quick charging of the power supply only in a case where the power supply temperature is in a fourth temperature range narrower than the third temperature range.

9. The inhalation component generating device disclosed in Item 7, wherein a lower limit temperature of the second temperature range is higher than a temperature at which an electrolytic solution or ionic liquid contained in the power supply coagulates.

10. The inhalation component generating device disclosed in Item 7, wherein a lower limit temperature of the third temperature range is higher than a temperature at which electrocrystallization occurs on an electrode of the power supply.

11. The inhalation component generating device disclosed in Item 3 or 4, wherein an upper limit temperature of the first temperature range is equal to or higher than an upper limit of the second temperature range, or is equal to or higher than an upper limit of the third temperature range.

12. The inhalation component generating device disclosed in any one of Items 1 to 11, wherein, in the process (a), the power supply temperature is acquired by detecting temperature of the power supply, the power supply temperature is estimated based on a value related to temperature of the power supply, or temperature of an object other than the power supply is detected, and the power supply temperature is estimated based on the output value.

13. The inhalation component generating device disclosed in any one of Items 1 to 12, further comprising: a power supply unit configured by storing the power supply in a case; and a cartridge unit that is attached to the power supply unit so as to be exchangeable.

14. A control circuit for controlling at least some of functions of an inhalation component generating device including a power supply and a load for evaporating or atomizing an inhalation component source by power from the power supply, wherein the control circuit is configured to perform: a process (a) of calculating power supply temperature based on an output of a temperature sensor; and a process (b1) of determining whether the power supply temperature is in a first temperature range, and performing deterioration diagnosis of the power supply only in a case where the power supply temperature is in the range.

15. A control method of an inhalation component generating device including a power supply, a load for evaporating or atomizing an inhalation component source by power from the power supply, and a temperature sensor, the control method comprising: a step (a) of calculating power supply temperature based on a detection result of the temperature sensor; and a step (b1) of determining whether the power supply temperature is in a first temperature range, and performing deterioration diagnosis of the power supply only in a case where the power supply temperature is in the range.

16. An inhalation component generating device comprising: a power supply; a load that evaporates or atomizes an inhalation component source by power from the power supply; and a control circuit that performs control based on the basis an output of a temperature sensor, wherein the control circuit is configured to be able to perform a plurality of functions of changing a residual amount of the power supply, including discharge, and determine whether to perform each of the plurality of functions, based on the output of the temperature sensor, and a temperature range in which performance of the discharge is allowed is wider than temperature ranges in which the other functions included in the plurality of functions are allowed.

17. A control method of an inhalation component generating device which includes a power supply, a load that evaporates or atomizes an inhalation component source by power from the power supply, and a control circuit that performs control based on an output of a temperature sensor and that can perform a plurality of functions of changing a residual amount of the power supply, including discharge, the control method comprising: a step of determining whether to perform each of the plurality of functions, based on the output of the temperature sensor, wherein a temperature range in which performance of the discharge is allowed is wider than temperature ranges in which the other functions included in the plurality of functions are allowed.

18. An inhalation component generating device comprising: a power supply; a load that evaporates or atomizes an inhalation component source by power from the power supply; and a control circuit that performs control based on an output of a temperature sensor, wherein the control circuit is configured to be able to perform a plurality of functions of changing a residual amount of the power supply, including deterioration diagnosis of the power supply, and determine whether to perform each of the plurality of functions, based on the output of the temperature sensor, and a temperature range in which the deterioration diagnosis is allowed is narrower than temperature ranges in which the other functions included in the plurality of functions are allowed.

19. The inhalation component generating device disclosed in Item 15, further comprising: a current sensor that outputs a charging/discharge current value of the power supply, or a voltage sensor that outputs an output voltage value of the power supply, wherein the control circuit is configured to perform the deterioration diagnosis based on an output value of the current sensor or the voltage sensor at any one of a timing in a course of discharge of the power supply, a timing immediately before discharge, a timing immediately after discharge, a timing in a course of charging, a timing immediately before charging, and a timing immediately after charging.

20. A control method of an inhalation component generating device which includes a power supply, a load that evaporates or atomizes an inhalation component source by power from the power supply, and a control circuit that performs control based on an output of a temperature sensor and that can perform a plurality of functions of changing a residual amount of the power supply, including deterioration diagnosis of the power supply, the control method comprising: a step of determining whether to perform each of the plurality of functions, based on the output of the temperature sensor, wherein a temperature range in which the deterioration diagnosis is allowed is narrower than temperature ranges in which the other functions included in the plurality of functions are allowed.

21. A control program for making an inhalation component generating device perform the control method disclosed in Item 15, 17, or 20.

This application also discloses, for example, inventions obtained by changing some expressions in the contents disclosed as product inventions to expressions of methods, computer programs, and computer program media

What is claimed is:

1. An inhalation component generating device, comprising:
   a power supply;
   a load that evaporates or atomizes an inhalation component source by power from the power supply;
   a control circuit that performs control based on an output of a temperature sensor and a sensor which outputs a generation request of an inhalation component; and
   a current sensor that outputs a charging/discharge current value of the power supply or a voltage sensor that outputs an output voltage value of the power supply,
   wherein the control circuit performs:
      a process (a) of calculating power supply temperature based on the output of the temperature sensor;
      a process (b1) of determining whether the power supply temperature is in a first temperature range, and performing deterioration diagnosis on the power supply only in a case where the power supply temperature is in the range;
      a process (b2) of performing the process (b1) in response to detection of the generation request; and
      a process (c1) of determining whether the power supply temperature is in a second temperature range in which discharge of the power supply is allowed, or whether the power supply temperature is in a third temperature range in which charging of the power supply is allowed, prior to the process (b1),
   wherein the control circuit is configured to perform the deterioration diagnosis based on an output value of the current sensor or the voltage sensor at any one of a timing in a course of discharge of the power supply, a timing immediately before discharge, a timing immediately after discharge, a timing in a course of charging, a timing immediately before charging, and a timing immediately after charging.

2. The inhalation component generating device according to claim 1, wherein
   the control circuit is configured to perform the process (b1) only in a case where the determination in the process (c1) is positive.

3. The inhalation component generating device according to claim 1, wherein
   the second temperature range or the third temperature range is wider than the first temperature range, and includes the first temperature range.

4. The inhalation component generating device according to claim 1, wherein
   an upper limit temperature of the first temperature range is lower than a temperature at which change of a structure or composition of an electrode of the power supply might occur.

5. The inhalation component generating device according to claim 1, wherein
   a lower limit temperature of the first temperature range is higher than a lower limit of the second temperature range, or is higher than a lower limit of the third temperature range.

6. The inhalation component generating device according to claim 5, wherein
   the control circuit is configured to be able to further perform quick charging of the power supply only in a case where the power supply temperature is in a fourth temperature range narrower than the third temperature range.

7. The inhalation component generating device according to claim 5, wherein
   a lower limit temperature of the second temperature range is higher than a temperature at which an electrolytic solution or ionic liquid contained in the power supply coagulates.

8. The inhalation component generating device according to claim 5, wherein
   a lower limit temperature of the third temperature range is higher than a temperature at which electrocrystallization occurs on an electrode of the power supply.

9. The inhalation component generating device according to claim 1, wherein
   an upper limit temperature of the first temperature range is equal to or higher than an upper limit of the second temperature range, or is equal to or higher than an upper limit of the third temperature range.

10. The inhalation component generating device according to claim 1, wherein,
    in the process (a),
    the power supply temperature is acquired by detecting temperature of the power supply,
    the power supply temperature is estimated based on a value related to temperature of the power supply, or
    temperature of an object other than the power supply is detected, and the power supply temperature is estimated based on the output value.

11. The inhalation component generating device according to claim 1, further comprising:
    a power supply unit configured by storing the power supply in a case; and
    a cartridge unit that is attached to the power supply unit so as to be exchangeable.

* * * * *